(12) United States Patent
Shiina et al.

(10) Patent No.: US 10,711,306 B2
(45) Date of Patent: Jul. 14, 2020

(54) METHOD AND KIT FOR MULTIPLEX DNA TYPING OF HLA GENE

(71) Applicant: Genodive Pharma Inc., Kanagawa (JP)

(72) Inventors: Takashi Shiina, Kanagawa (JP); Shingo Suzuki, Kanagawa (JP); Yuki Wada, Kanagawa (JP); Shigeki Mitsunaga, Kanagawa (JP); Hidetoshi Inoko, Kanagawa (JP)

(73) Assignee: GENODIVE PHARMA INC., Kanagawa (JP)

( * ) Notice: Subject to any disclaimer, the term of this patent is extended or adjusted under 35 U.S.C. 154(b) by 274 days.

(21) Appl. No.: 14/786,690

(22) PCT Filed: May 9, 2014

(86) PCT No.: PCT/JP2014/062433
§ 371 (c)(1),
(2) Date: Oct. 23, 2015

(87) PCT Pub. No.: WO2014/181854
PCT Pub. Date: Nov. 13, 2014

(65) Prior Publication Data
US 2016/0060695 A1    Mar. 3, 2016

(30) Foreign Application Priority Data

May 9, 2013   (JP) ................................ 2013-099547

(51) Int. Cl.
*C12P 19/34*       (2006.01)
*C12Q 1/6881*      (2018.01)

(52) U.S. Cl.
CPC ..... *C12Q 1/6881* (2013.01); *C12Q 2600/156* (2013.01); *C12Q 2600/16* (2013.01)

(58) Field of Classification Search
CPC ............ C12Q 1/6881; C12Q 2600/156; C12Q 2600/16
USPC ...................................................... 435/91.2
See application file for complete search history.

(56) References Cited

U.S. PATENT DOCUMENTS

| 2007/0031846 | A1* | 2/2007 | Cargill ................. | C12Q 1/6883 435/6.14 |
| 2007/0065860 | A1 | 3/2007 | Hildebrand | |
| 2008/0020386 | A1* | 1/2008 | Chen .................... | C12Q 1/6883 435/6.12 |
| 2009/0208947 | A1* | 8/2009 | Wang ................... | C12Q 1/6853 435/6.12 |

FOREIGN PATENT DOCUMENTS

| CN | 101962676 | | 2/2011 |
| EP | 0892069 | | 1/1999 |
| EP | 0953650 | A1 | 11/1999 |
| EP | 2599877 | A1 | 6/2013 |
| EP | 2735617 | A1 | 5/2014 |
| EP | 3075863 | A1 | 10/2016 |
| JP | 11-216000 | | 8/1999 |
| JP | H11-216000 | | 8/1999 |
| JP | 2007312660 | A | 12/2007 |
| JP | 2009261358 | A | 11/2009 |
| JP | 2011-500041 | | 1/2011 |
| WO | 9215711 | A1 | 9/1992 |
| WO | WO2000061795 | | 10/2000 |
| WO | 2005042764 | A2 | 5/2005 |
| WO | WO2005042764 | | 5/2005 |
| WO | WO2009049889 | | 4/2009 |
| WO | 2011030159 | A1 | 3/2011 |
| WO | 2012000445 | A1 | 1/2012 |
| WO | 2014065410 | A1 | 5/2014 |
| WO | WO2013011734 | | 2/2015 |
| WO | 2015047220 | A2 | 4/2015 |
| WO | 2015080226 | A1 | 6/2015 |

OTHER PUBLICATIONS

Nelson et al. Genome Research 14(8), 1664-1668 (Year: 2004).*
Tiercy et al., human Immunology, 32 (2), 95-101 (Year: 1991).*
Tonnelle et al., EMBO J., 4 (11), 2839-2847 (Year: 1985).*
Hashemi-Tavoularis, Tissue Antigens 52 (3), 294-299 (Year: 1998).*
Shiina et al., Tissue Antigen, 80, 305-316, Aug. 4, (Year: 2012).*
International Search Report dated Jul. 29, 2014 for PCT/JP2014/062433.
Shingo, et al. "Jisedai Sequencer o Mochiita HLA Class I Idenshi no Cho Kokaizodo DNA Typing (Super high resolution Single molecule-Sequence Based Typing; SS-SBT) Ho no Kaihatsu", MHC, 2012, vol. 19, No. 1, 43-53.
Ozaki, et al. "Jisedai Sequencer o Mochiita HLA-DRB1 Idenshi no Cho Kokaizodo DNA Typing (Super high resolution Single molecule-Sequence Based Typing; SS-SBT) Ho no Kaihatsu", MHC, 2012, vol. 19, No. 211-221.

(Continued)

*Primary Examiner* — Cynthia B Wilder
(74) *Attorney, Agent, or Firm* — Pearne & Gordon LLP

(57) ABSTRACT

The purpose of the present invention is to provide a method and kit for highly precise DNA typing, in which a high throughput sequencer is used and ambiguity derived from phase ambiguity is eliminated. The present invention provides a method for the DNA typing of HLA, which is characterized by comprising: (1) a step of preparing sets of primers which respectively hybridize specifically to an upstream region and a downstream region of at least 2 genes selected from genes belonging to HLA class I and HLA class II in a human genome sequence, and are capable of amplifying under the same PCR conditions; (2) a step of simultaneously amplifying said at least 2 genes in a test sample (DNA) using the sets of primers in a single container under the same PCR conditions; (3) a step of determining the nucleotide sequences of PCR amplified products; and (4) a step of optionally carrying out a homology search within a database.

3 Claims, 12 Drawing Sheets
Specification includes a Sequence Listing.

(56) References Cited

OTHER PUBLICATIONS

Moonsamy, et al. "High throughput HLA genotyping using 454 sequencing and the Fluidigm Access Array System for simplified amplicon library preparation," Tissue Antigens, Mar. 2013, vol. 82, No. 3, 141-149.
Lind C., et al., "Next-generation sequencing: the solution for high-resolution, unambiguous human leukocyte antigen typing," Human Immunology, vol. 71, pp. 1033-1042 (2010).
Shiina T., et al., Tissue Antigens, vol. 80, pp. 305-316, 2012.
"Experimental Medicine", vol. 27, No. 1, 2009 (Yodo-sha).
Office Action dated Feb. 19, 2014 for U.S. Appl. No. 14/233,909.
Chinese Office Action dated Nov. 15, 2014 for Application No. 201280036108.5.
Gabriel, et al. "Rapid high-throughput human leukocyte antigen typing by massively parallel pyrosequencing for high-resolution allele identification." Human Immunology, 70 (2009), pp. 960-964.
Zhu, et al. "Analysis of the complete genomic sequence of HLA-A alleles in the Chinese Han population," International Journal of Immunogenetics 26, 2009, 351-360.
Lowe, et al. "A computer program for selection of oligonucleotide primers for polymerase chain reactors." Neucleic Acids Research, vol. 18, No. 7, Mar. 2, 1990, pp. 1757-1761.
Inoko, et al. "Transplantation/transfusion Examination", Kodan-sha Scientific, 2004.
Seurynck K. et al., Use of 3' and 5' 1-35, Untranslated Region Polymorphism of Class I HLA-B to Determine Full Length Nucleotide Sequences, Human Immunology, 1997, vol. 55, No. Suppl. 1, p. 28.
Liu X. et al., Catalog of 162 single nucleotide 1-35 polymorphisms (SNPs) in a 4.7-kb region of the HLA-DP loci in southern Chinese ethnic groups, Journal of Human Genetics, 2004, vol. 49, p. 73-79.
Zhu F. et al., Analysis for complete genomic sequence of HLA-B and HLA-C alleles in the Chinese Han population, International Journal of Immunogenetics, May 17, 2011 (published online), vol. 38, pp. 281-284.
Bentley, et al. "High-resolution, high-throughput HLA genotyping by next-generation sequencing." Tissue Antigens, vol. 74, Jul. 18, 2009, p. 393-403.
*Homo sapiens* major histocompatibility complex, class I,A (HLA-A) RefSeqGene on Chromosome 6, p. 1-16.
Magor, et al. "Natural Inactivation of a Common HLA Allele (A*2402) Has Occurred on at Least Three Separate Occasions." American Association of Immunologists, Journal of Immunology,1997, p. 5242-5250.
"*Homo sapiens* MHC leukocyte antigen (HLA-A) gene, HLA-A*2402 allele, complete cds." p. 1-8.
"*Homo sapiens* chromosome 6 genomic contig, GRCh27.p13 Primary Assembly." p. 1-11.
Dunn, et al. "DNA Sequencing as a Tissue-Typing Tool." Methods in Molecular Medicine, vol. 91, Pediatric Hematology: Methods and Protocols, p. 233-246.
Salome, et al. "Full-length sequence analysis of the HLA-DRB1 locus suggests a recent origin of alleles." Immunogenetics, 59 (2007), 261-271.
European Search Report issued in Application No. 14795192.5 dated Jan. 23, 2017, pp. 1-20.
Toshio, et al., Clinical Microbiology, vol. 31, No. 2, pp. 111-115, 2004. See tables in English.
Ohkusu et al., JapJChem, vol. 59, No. 5, pp. 441-453,2011. English abstract provided.
Suzuki et al., "Development of super high resolution single molecule—sequence based typing (SS-SBT) method for HLA class I genes," MHC vol. 19, No. 1, pp. 43-54, 2012. (English abstract provided).
Ozaki et al., "Development of super high resolution single molecule sequence based typing (SS-SBT) method in HLA-DRB1 gene by next generation sequencing," MHC vol. 19, No. 2, pp. 211-222, 2012. (English abstract provided).
Moonsamy et al., "High throughput HLA genotyping using 454 sequencing and the Fluidigm Access Array System for simplified amplicon library preparation," Tissue Antigens, vol. 81, No. 3, pp. 141-149, Mar. 2013.
Shiina et al., "Super high resolution for single molecule-sequence-based typing of classical HLA loci at the 8-digit level using next generation sequencers", Tissue Antigens, vol. 80, pp. 305-316, 2012.

* cited by examiner

[fig.1]
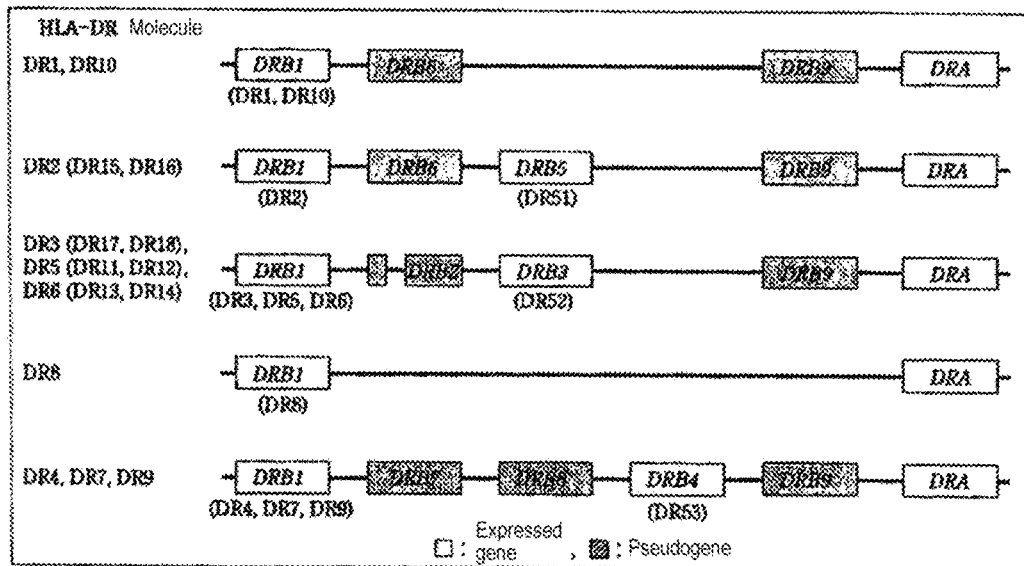
[fig.2]
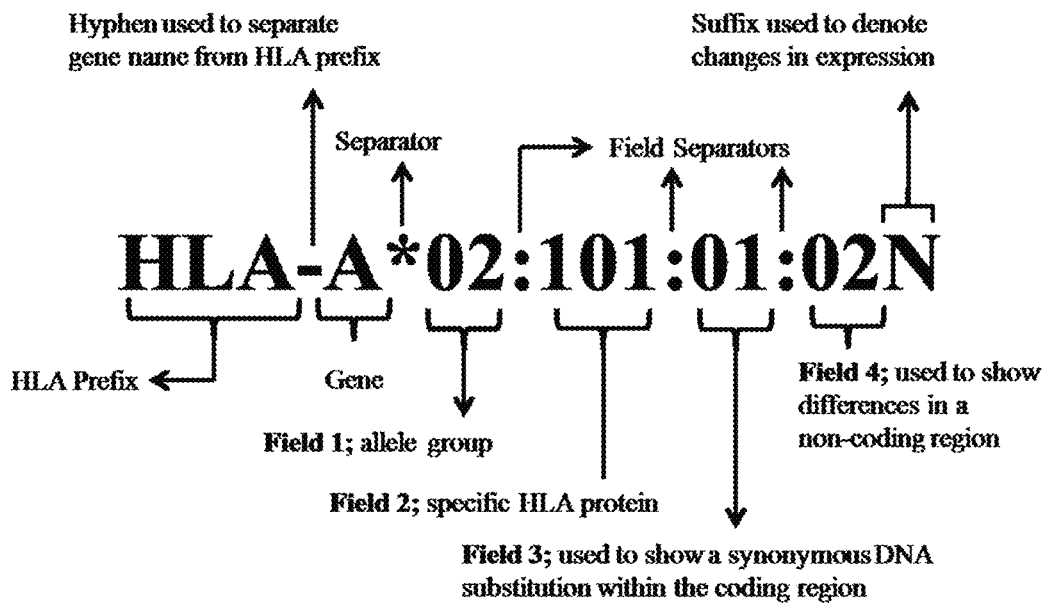

1.0% agarose gel; 2 ul of PCR products is applied; M: 1kb ladder

Fig. 7

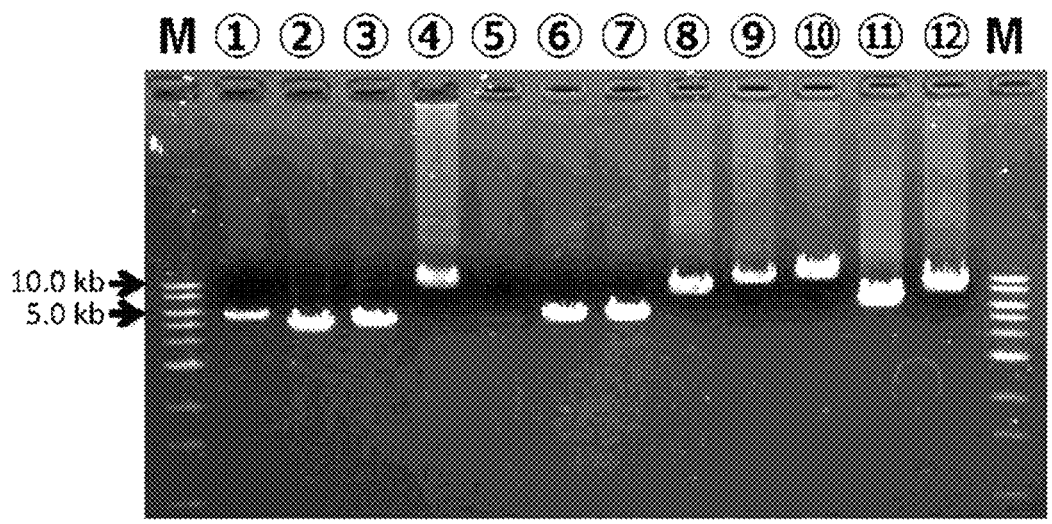

1.0% agarose gel; 2 ul of PCR products is applied; M: 1kb ladder

Notes regarding lanes:
① HLA-A (see Table 1; SEQ ID Nos. 1 to 3)
② HLA-B (see Table 1; SEQ ID Nos. 4 and 5)
③ HLA-C (see Table 1; SEQ ID Nos. 6 to 8)
④ HLA-DRB1-1 (see Patent Document 3)
⑤ HLA-DRB1-2 (see Patent Document 3 and Table 2; SEQ ID Nos. 9 to 12)
⑥ HLA-DRB3 (see Table 2; SEQ ID Nos. 13 to 15)
⑦ HLA-DRB4 (see Table 2; SEQ ID Nos. 16 and 17)
⑧ HLA-DQA1 (see Table 2; SEQ ID Nos. 20 and 21)
⑨ HLA-DQB1 (see Table 2; SEQ ID Nos. 22 to 26)
⑩ HLA-DPA1 (see Table 2; SEQ ID Nos. 27 to 29)
⑪ HLA-DPB1-1 (see Patent Document 3)
⑫ HLA-DPB1-2 (see Table 2; SEQ ID Nos. 30 and 31)

Fig.8

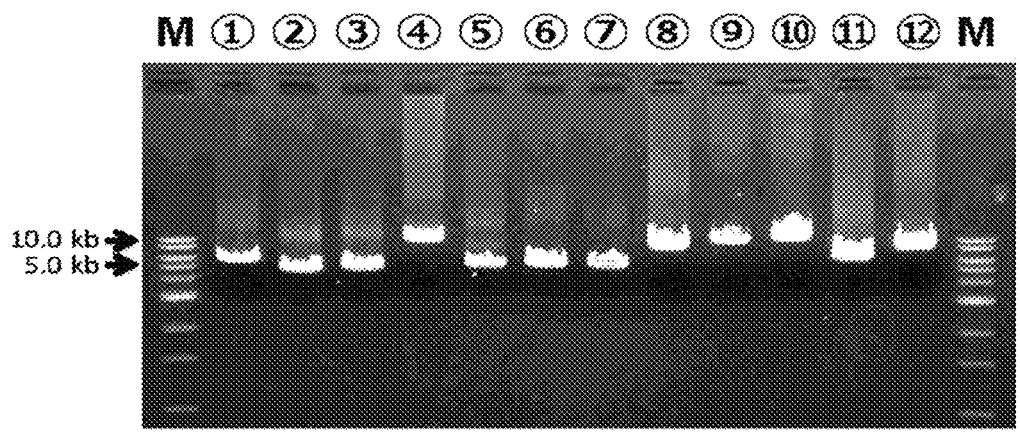

1.0% agarose gel; 2 ul of PCR products is applied; M: 1kb ladder

Notes regarding lanes:
① HLA-A (see Table 1; SEQ ID Nos. 1 to 3)
② HLA-B (see Table 1; SEQ ID Nos. 4 and 5)
③ HLA-C (see Table 1; SEQ ID Nos. 6 to 8)
④ HLA-DRB1-1 (see Patent Document 3)
⑤ HLA-DRB1-2 (see Patent Document 3 and Table 2; SEQ ID Nos. 9 to 12)
⑥ HLA-DRB3 (see Table 2; SEQ ID Nos. 13 to 15)
⑦ HLA-DRB4 (see Table 2; SEQ ID Nos. 16 and 17)
⑧ HLA-DQA1 (see Table 2; SEQ ID Nos. 20 and 21)
⑨ HLA-DQB1 (see Table 2; SEQ ID Nos. 22 to 26)
⑩ HLA-DPA1 (see Table 2; SEQ ID Nos. 27 to 29)
⑪ HLA-DPB1-1 (see Patent Document 3)
⑫ HLA-DPB1-2 (see Table 2; SEQ ID Nos. 30 and 31)

Fig.9

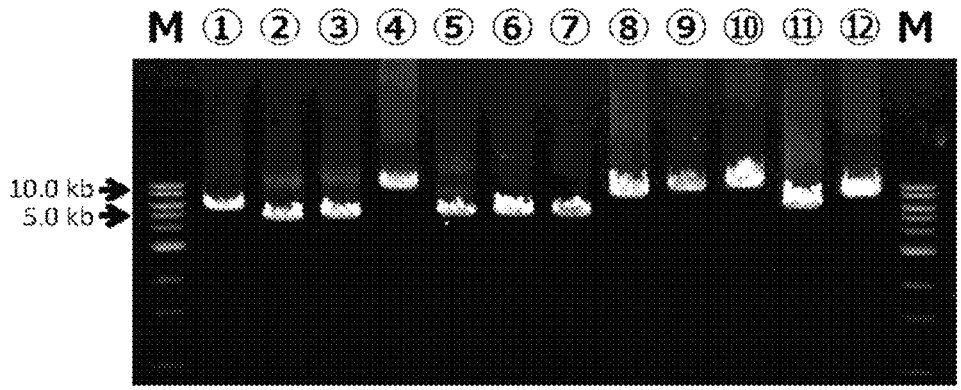

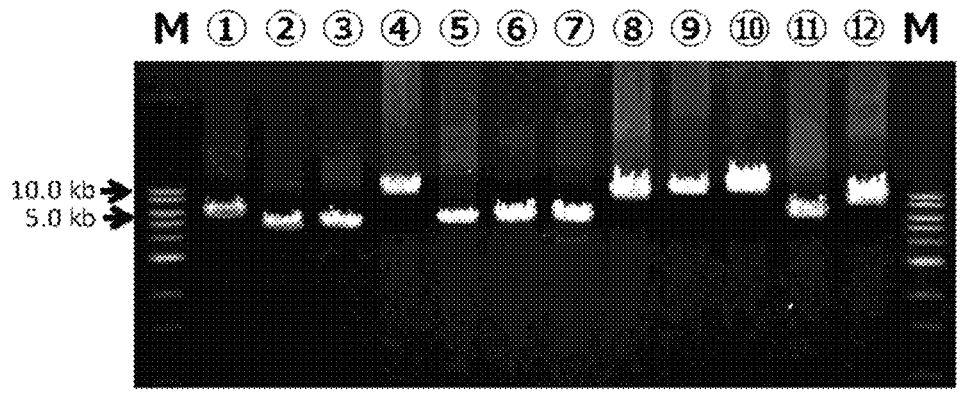

1.0% agarose gel; 2 ul of PCR products is applied; M: 1kb ladder

Notes regarding lanes:
① HLA-A (see Table 1; SEQ ID Nos. 1 to 3)
② HLA-B (see Table 1; SEQ ID Nos. 4 and 5)
③ HLA-C (see Table 1; SEQ ID Nos. 6 to 8)
④ HLA-DRB1-1 (see Patent Document 3)
⑤ HLA-DRB1-2 (see Patent Document 3 and Table 2; SEQ ID Nos. 9 to 12)
⑥ HLA-DRB3 (see Table 2; SEQ ID Nos. 13 to 15)
⑦ HLA-DRB4 (see Table 2; SEQ ID Nos. 16 and 17)
⑧ HLA-DQA1 (see Table 2; SEQ ID Nos. 20 and 21)
⑨ HLA-DQB1 (see Table 2; SEQ ID Nos. 22 to 26)
⑩ HLA-DPA1 (see Table 2; SEQ ID Nos. 27 to 29)
⑪ HLA-DPB1-1 (see Patent Document 3)
⑫ HLA-DPB1-2 (see Table 2; SEQ ID Nos. 30 and 31)

1.0% agarose gel; 2ul of PCR product is applied; M: 1kb ladder
Notes regarding lanes:
①A
②B
③C
④DRB1-1 (5'UTR to Exon 2)
⑤DRB1-2 (Exon 2 to 3'UTR)
⑥Sample 1: DRB4; Sample 2: DRB3; Sample 3: DRB3; Sample 4: DRB3
⑦Sample 1: DRB5; Sample 2: DRB4; Sample 3: DRB5; Sample 4: DRB4
⑧DQA1
⑨DQB1
⑩DPA1
⑪DPB1-1 (5'UTR to Exon 2)
⑫DPB1-2 (Exon 2 to 3'UTR)

1.0% agarose gel; 2ul of PCR product is applied; M: 1kb ladder

Notes regarding lanes:
①HLA-A
②HLA-B
③HLA-C
④HLA-DRB1-2 (Exon 2 to 3'UTR)
⑤mixture of ① to ④

Fig. 13

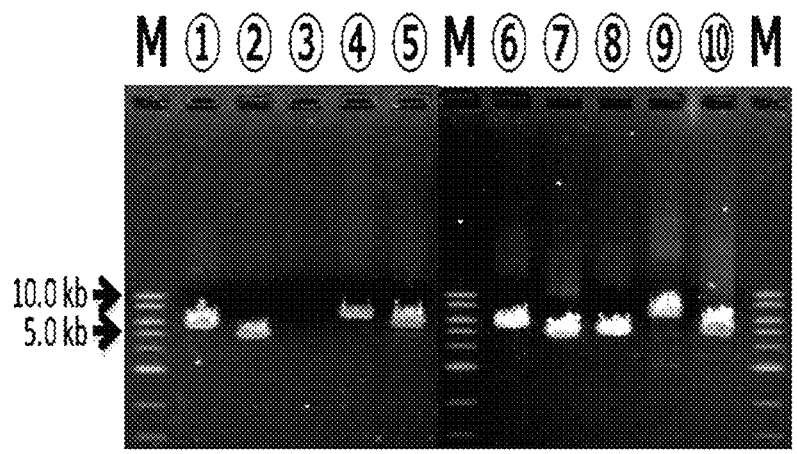

Notes regarding lanes:
① Previously developed HLA-A primer set
② Previously developed HLA-B primer set
③ Previously developed HLA-C primer set
④ Previously developed HLA-DRB1 primer set
⑤ Previously developed multiplex primer sets (HLA-A, -B, -C, -DRB1)
⑥ Newly developed HLA-A primer set
⑦ Newly developed HLA-B primer set
⑧ Newly developed HLA-C primer set
⑨ Newly developed HLA-DRB1 primer set
⑩ Newly developed multiplex primer sets (HLA-A, -B, -C, -DRB1)

METHOD AND KIT FOR MULTIPLEX DNA TYPING OF HLA GENE

REFERENCE TO A SEQUENCE LISTING, A TABLE, OR A COMPUTER PROGRAM LISTING APPENDIX SUBMITTED AS AN ASCII TEXT FILE

The material in the ASCII text file, named WING2-55245-Seq.txt, created Oct. 22, 2015, file size 6.25 KB, is hereby incorporated by reference.

TECHNICAL FIELD

The present invention relates to a method for super high resolution multiplex DNA typing of a HLA gene using a high throughput DNA sequencer.

BACKGROUND ART

The human leucocyte antigen (HLA), which represents major human histocompatibility complex (MHC), presents peptides derived from foreign proteins such as pathogens and peptides derived from self-proteins to T cells. In this manner, HLA is deeply involved in induction of immunological responses. As major HLAs, six types of antigens are known, namely, class I antigens (HLA-A, HLA-B, HLA-C), which is expressed in almost all cells, and class II antigens (HLA-DR, HLA-DQ, HLA-DP), which is expressed mainly in immune cells.

The HLA class I antigen consists of a highly polymorphic α chain and a substantially non-polymorphic β2-microglobulin; whereas the HLA class II antigen consists of a highly polymorphic β chain and a less polymorphic α chain. The α chains of class I antigens are encoded by HLA-A, HLA-B and HLA-C genes. The β chains of class II antigens are encoded by HLA-DRB1, HLA-DRB3/4/5, HLA-DQB1 and HLA-DPB1 genes, whereas the α chains are encoded by HLA-DRA1, HLA-DQA1 and HLA-DPA1 genes. In a gene level, in HLA class I antigens, exon 2 and exon 3 of a gene encoding an α chain are highly polymorphic; whereas, in HLA class II antigens, exon 2 of a gene encoding a β chain is highly polymorphic.

A gene region encoding a HLA is located on short arm of human chromosome 6 at 6p21.3. A Class I region (HLA-A, HLA-B and HLA-C, etc.), a class III region and a class II region (HLA-DRA, HLA-DRB1, HLA-DRB3/4/5, HLA-DQA1, HLA-DQB1, HLA-DPA1, HLA-DPB1, etc.) are arranged in this order from the telomere side toward the centromere side. Many genes are encoded at an extremely high density and association of these genes with transfusion, transplantation and various diseases have been reported. In the class III region, no HLA genes are present and genes of complement components and tumor necrosis factors (TNF), etc. are present.

In a HLA-DRB gene region encoding a β chain of a HLA-DR antigen, it has been confirmed that 5 types of structural polymorphisms are present. In DR1 type and DR10 type, pseudogenes such as HLA-DRB6 and HLA-DRB9 in addition to HLA-DRB1 are located on the same haplotype. In DR2 type, a HLA-DRB5 (DR51) gene and pseudogenes such as HLA-DRB6 and HLA-DRB9 in addition to HLA-DRB1 are located on the same haplotype. In DR3, DR5 and DR6 types, a HLA-DRB3 (DR52) gene and pseudogenes such as HLA-DRB2 and HLA-DRB9 in addition to HLA-DRB1 are located on the same haplotype. In DR4, DR7 and DR9 types, a HLA-DRB4 (DR53) gene and pseudogenes such as HLA-DRB7, HLA-DRB8 and HLA-DRB9 in addition to HLA-DRB1 are located on the same haplotype. In contrast to these, in DR8 type, no HLA-DRB genes except HLA-DRB1 are located on the same haplotype (FIG. 1).

In the exon of each HLA gene, regions having an abundance of polymorphism (polymorphic regions) are present. In many cases, a nucleotide sequence (amino acid sequence) present in a certain polymorphic region is commonly present in a plurality of HLA alleles. In short, each HLA allele is specified by a plurality of polymorphic regions in combination. In a HLA class I antigen, not only a polymorphic region in the exon but also exon 2 or exon 3 having the same nucleotide sequence is sometimes commonly present in a plurality of alleles.

Since a highly polymorphic region is present in a HLA, the number of types of HLA alleles is known to be extremely large and notation of them has been defined: i.e., a first field (two-digit level) is for discrimination of serologic HLA types, a second field (4-digit level) is for discrimination of alleles having an amino acid substitution in the same serologic HLA type, a third field (6-digit level) is for discrimination of alleles having a base substitution not accompanying an amino acid mutation and a fourth field (8-digit level) is for discrimination of alleles having a base substitution in an intron, which is out of the genetic region encoding a HLA molecule (FIG. 2).

In bone marrow transplantation, it is said that if the HLA type (HLA-A, HLA-B, HLA-C, HLA-DRB1) of a patient seeking to receive a transplant completely matches the HLA type of a donor at a 4-digit level, the success rate of transplantation improves and a severe graft versus host disease (GVHD) frequency reduces. Conversely, if the HLA types do not match at a 4 digit level, a risk of causing a failure such as a rejection response increases. Accordingly, accurate and highly precise HLA typing is extremely important also in a clinical point of view.

As a method for DNA typing in a HLA gene, a SBT (sequence based typing) method and a SSO (Sequence Specific Oligonucleotide)—Luminex method based on a polymerase chain reaction (PCR) are in mainstream.

These conventional DNA typing methods have an advantage in that typing of many samples is quickly performed; however, sometimes fail to accurately determine a polymorphic region and cis/trans positional relationship of exons on a chromosome in the case of a class I gene. Because of this, phase ambiguity occurs, highly precise HLA typing was sometimes not easily performed.

Since the conventional methods are DNA typing methods using PCR mainly based on exon regions of each HLA gene, base substitutions in an intron region and a promoter region are overlooked, with the result that there was a risk of failure in detection of a null allele, which has the same gene structure as other HLA expressing genes but is suppressed in expression.

For example, since the PCR conditions for each HLA gene are not same, the PCR for each HLA gene must be independently performed, thus, according to the method described in the Patent Document 1, an accelerated and simplified operation is not achieved.

The present inventors offered a highly precise DNA typing method capable of eliminating phase ambiguity by using a set of primers which respectively anneal specifically to an upstream region and a downstream region of each HLA gene locus (Patent Document 2 and Non Patent Document 2). However, since even in the method the PCR conditions for each gene locus are not completely unified, a multiple method in which PCR for all of the gene loci are simultaneously performed has never been achieved.

Furthermore, even though the acceleration of PCT is expected, a high-speed PCR apparatus in which the time required for the rise and fall of the temperature during the PCR is drastically reduced, has never been considered.

RELATED ART

Patent Document

Patent Document 1: JP H11-216000 A
Patent Document 2: WO 2013/011734

Non Patent Document

Non Patent Document 1: Lind C., et al., Human Immunology, Vol. 71, Pages 1033-1042, 2010
Non Patent Document 2: Shiina T., et al., Tissue Antigens, Vol. 80, Pages 305-316, 2012

SUMMARY OF INVENTION

Technical Problem

An object of the present invention is to unify the PCR conditions (for example, annealing temperature) for the HLA genes including HLA-DRB3/DRB4/DRB5 newly designed as a gene-specific primer and develop a multiplex PCR method capable of simultaneously PCR amplifying HLA genes in a single container under the conditions. Also, it is to provide a super high resolution multiplex DNA typing method in which ambiguity derived from phase ambiguity can be eliminated and an accelerated and simplified operation can be achieved by designing the PCR conditions (for example, the time required for extension reaction) for a multiplex PCR method using a high-speed PCR apparatus.

Solution to Problem

As a result of performing diligent research in order to solve the above-described problems, the present inventors discovered that HLA genes can be PCR amplified under the same conditions, irrespective of the kind of HLA genes, by re-designing a set of primers for each HLA gene and selecting a DNA polymerase, thereby achieving the present invention.

In other words, the present invention provides a method for DNA typing of HLA, including the following steps:

(1) a step of preparing sets of primers which respectively hybridize specifically to an upstream region and a downstream region of at least two genes selected from genes belonging to HLA class I and class II in a human genome nucleotide sequence, and amplify under the same PCR conditions;

(2) a step of amplifying at least two genes from a test sample (DNA) at the same time under the same PCR conditions in a single container using the sets of primers;

(3) a step of determining the nucleotide sequences of PCR products; and (4) optionally, a step of carrying out a homology search within a database.

Effects of the Invention

The present invention has solved the above problems of the prior art by designing sets of PCR primers which can specifically bind and amplify HLA genes, especially HLA class I antigens such as HLA-A, HLA-B and HLA-C and HLA class II antigens such as HLA-DRB1, HLA-DRB3/4/5, HLA-DQA1, HLA-DQB1, HLA-DPA1 and HLA-DPB1 under the same annealing temperature, selecting a DNA polymerase preferable for the present DNA typing method, setting preferable PCR conditions in which DNA typing for all of the HLA genes can be simultaneously performed on one PCR apparatus when said enzyme is used, developing a multiplex PCR method for HLA-A, HLA-B, HLA-C and HLA-DRB1, setting a time required for an extension reaction in the multiplex PCR when a high-speed PCR apparatus is used, and/or using high throughput sequencing techniques.

The method of the present invention, since it provides all nucleotide sequences required for DNA typing of a HLA gene from a single molecule, is an ultimate DNA typing method in which phase ambiguity due to unclear cis/trans positional relationship is eliminated. Owing to this, highly precise matching of HLAs between a patient seeking to receive a transplant and a donor candidate upon transplantation is realized.

Since all nucleotide sequences of a HLA gene including the peripheral regions such as a promoter region, exon regions and intron regions are determined, a null allele, which is suppressed in expression, and a novel allele can be detected.

Since the preferable PCR conditions, in which DNA typing of more than one or all of HLA genes can be simultaneously performed on one PCR apparatus, are provided according to the present invention, a PCR operation is accelerated and simplified.

Since a multiplex PCR method of more than one HLA genes is provided according to the present invention, more precise and rapid typing of HLAs between a transplant applicant and a donor candidate is achieved.

BRIEF DESCRIPTION OF DRAWINGS

FIG. 1 A diagram showing a HLA-DR gene region, cited from "Transplantation/transfusion Examination", supervised by Hidetoshi Inoko, Takehiko Sasazuki and Takeo Juuji, Kodan-sha Scientific, 2004, page 48.

FIG. 2 A diagram showing a classification of HLA alleles, cited from the IMGT-HLA database (www.ebi.ac.uk/ipd/imgt/hla/).

FIG. 7 An agarose gel electrophoretic pattern showing PCR states of HLA genes amplified in Example 1.

FIG. 8 An agarose gel electrophoretic pattern showing PCR states of HLA genes amplified in Example 2.

FIG. 9 An agarose gel electrophoretic pattern showing PCR states of HLA genes amplified in Example 3.

FIG. 13 An agarose gel electrophoretic pattern showing PCR states of HLA-A, HLA-B, HLA-C and HLA-DRB1 genes amplified in Comparative Example 1.

MODES FOR CARRYING OUT THE INVENTION

Now, the DNA typing method of the present invention will be more specifically described step by step.

(1) Step of Preparing a Primer Set

In the DNA typing method of the present invention, first, sets of primers which comprehensively PCR amplify a region from an upstream region to a downstream region of each of HLA-A, HLA-B, HLA-C, HLA-DQA1, HLA-DQB1 and HLA-DPA1 genes, and a region from a 5' untranslated region to exon 2 and a region from exon 2 to a 3' untranslated region of each of HLA-DRB1 and HLA-DPB1 genes as well as a region from exon 2 to a 3' untranslated region of HLA-DRB3/4/5 in the human genome sequence and can anneal under the same conditions are prepared.

Figure 3:
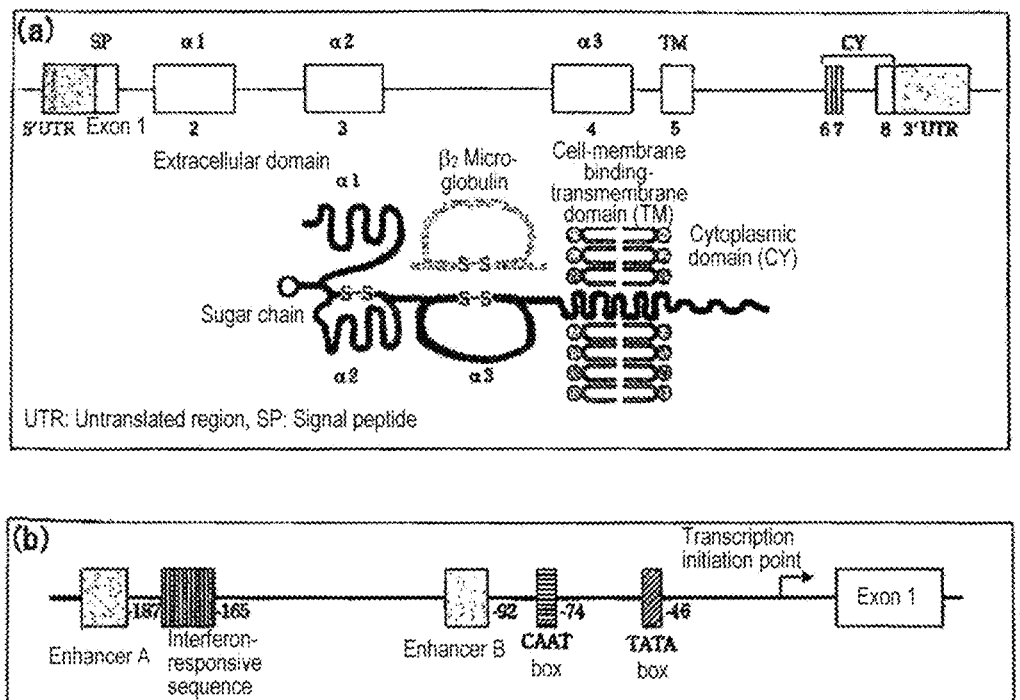
FIG. 3 (a) A diagram showing the relationship between the structure of a HLA class I gene and the structure of HLA class I molecule; and (b) A diagram showing the structure of a promoter region of a HLA class I gene, cited from "Transplantation/transfusion Examination", supervised by Hidetoshi Inoko, Takehiko Sasazuki and Takeo Juuji, Kodan-sha Scientific, 2004, page 35.
Figure 5:
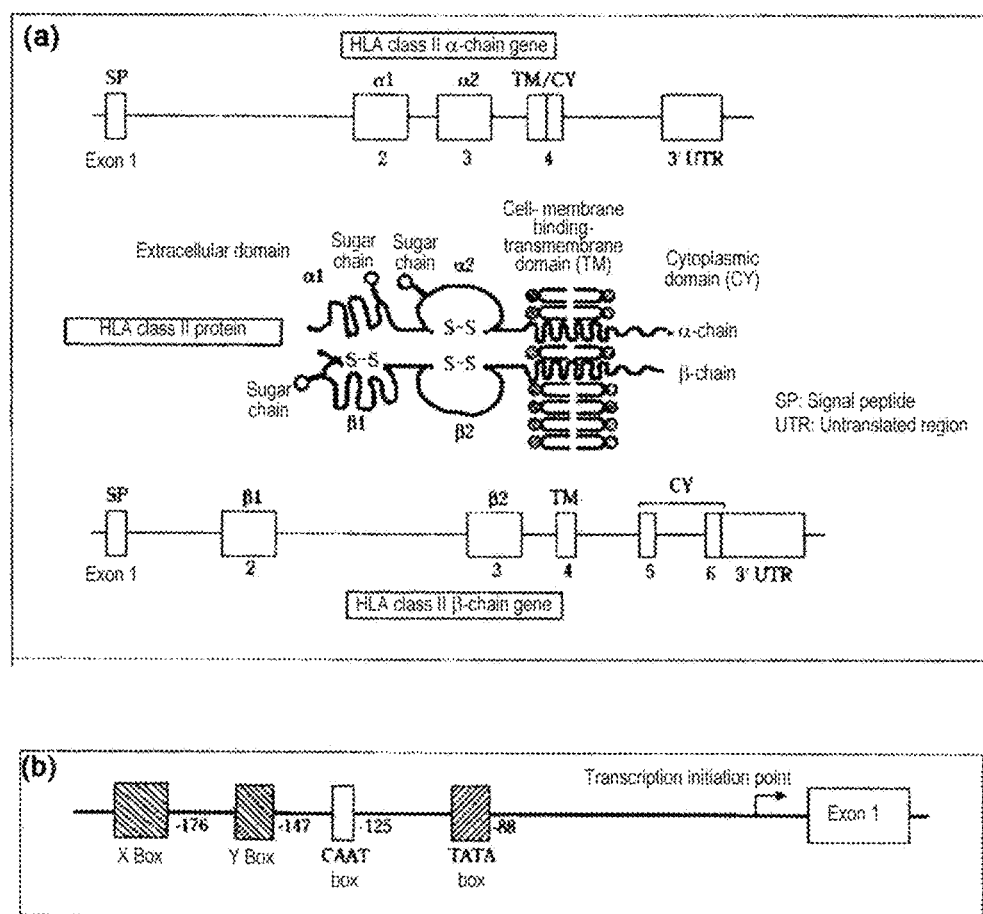
FIG. 5 (a) A diagram showing the relationship between the structure of a HLA class II gene and the structure of HLA class II molecule; and (b) A diagram showing the structure of a promoter region of a HLA class II gene, cited from "Transplantation/transfusion Examination", supervised by Hidetoshi Inoko, Takehiko Sasazuki and Takeo Juuji, Kodan-sha Scientific, 2004, pages 46 and 47.

The genome sequence of human chromosome 6 (6p21.3) in which a HLA gene is present has been already elucidated and association between the gene structure and the structure of an expression product (HLA antigen) has been known (see FIG. 3 and FIG. 5).

More specifically, genes of HLA-A, HLA-B and HLA-C, which specify classic HLA class I antigens, each contains 8 exons (FIG. 3(a)). Outside of exon 1, two types of enhancers and a promoter region are present to control expression (FIG. 3 (b)).

It is further known that many polymorphic regions are present in exon 2, 3 and 4. Thus, PCR was performed by using primers designed particularly based on exon 2 and 3 in conventional DNA typing methods. Accordingly, a problem of phase ambiguity has occurred as mentioned above.

In the meantime, the genes of HLA-DR, HLA-DQ and HLA-DP, which specify classic HLA class II antigens, consist of α chains and β chains, whose genes each contain 5 to 6 exons (FIG. 5 (a)). Outside of exon 1, a promoter region is present to control expression (FIG. 5 (b)).

Figure 4:
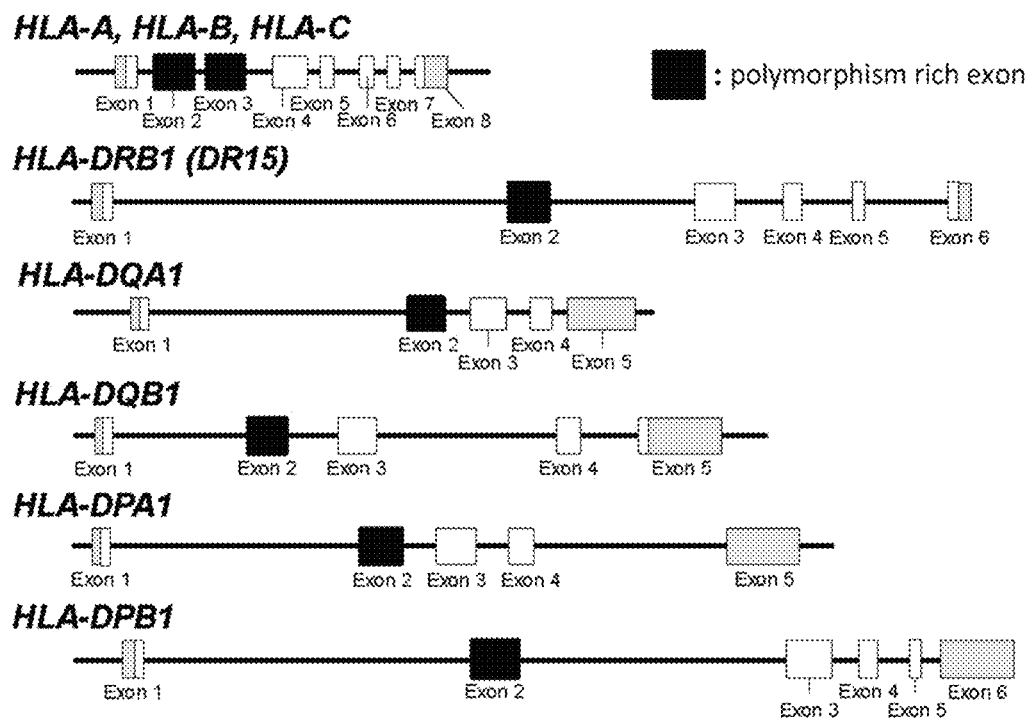
FIG. 4 A diagram showing the structure of each HLA gene.

It is further known that many polymorphic regions are present in exons 2 and 3. Thus, PCR was performed by using primers designed particularly based on exon 2 in conventional DNA typing methods. Accordingly, a problem of phase ambiguity occurred as mentioned above (FIG. 4).

In the present invention, a set of primers which can PCR amplify all regions of a gene (including not only exons but also introns, 5' and 3' untranslated regions and a promoter region) in each of classic class I antigens (HLA-A, HLA-B, HLA-C) and classic class II antigens (HLA-DRB1, HLA-DQA1, HLA-DQB1, HLA-DPA1 and HLA-DPB1); and/or a set of primers which can PCR amplify a region of exon 2 to a 3' untranslated region in HLA-DRB3/4/5 are prepared, and PCR products obtained by PCR amplification using the sets of primers are subjected to high throughput sequencing (described later). Therefore, uncertainty such as phase ambiguity can be eliminated and the presence or absence of a null allele can be accurately detected.

Specifically, sets of primers corresponding to at least two genes selected from PCR primer sets listed in Table 1 to Table 3 below are prepared.

At least two genes refers to at least two genes selected from the group consisting of HLA-A, HLA-B, HLA-C, HLA-DQA1, HLA-DQB1, HLA-DPA1, HLA-DRB1 and HLA-DPB1. It includes combinations of two, three, four, five, six or seven genes selected from the group consisting of HLA-A, HLA-B, HLA-C, HLA-DQA1, HLA-DQB1, HLA-DPA1, HLA-DRB1 and HLA-DPB1 as well as a combination of all the eight genes.

The primer sets corresponding to each gene will be described below.

In Table 1, SEQ ID NOS: 1 to 3 represent a set of PCR primers specifically amplifying a HLA-A gene, which is an α chain of MHC class I. These primers of the set are nucleotide sequences located at positions, which correspond to the upstream and downstream of all regions of a HLA-A gene (including promoter, exons and introns) and sandwich the all regions, in the human genome sequence (Reference sequence: hg19).

SEQ ID NO: 1 or 2 has a nucleotide sequence corresponding to the 29,909,483rd position to the 29,909,514th position in a human genome sequence (Reference sequence: hg19).

SEQ ID NO: 3 has a complementary nucleotide sequence to a nucleotide sequence corresponding to the 29,914,925th position to the 29,914,954th position in a human genome sequence (Reference sequence: hg19).

The length of a PCR product obtained by using these primer sets is estimated as about 5,500 bases (bp).

In Table 1, SEQ ID NOS: 4 and 5 represent a set of PCR primers specifically amplifying a HLA-B gene, which is an α chain of MHC class I. These primers of the set are nucleotide sequences located at positions, which correspond to the upstream and downstream of all regions of a HLA-B gene (including promoter, exons and introns) and sandwich the all regions, in the human genome sequence (Reference sequence: hg19).

SEQ ID NO: 4 has a complementary nucleotide sequence to a nucleotide sequence corresponding to the 31,325,796th position to the 31,325,824th position in a human genome sequence (Reference sequence: hg19).

SEQ ID NO: 5 has a nucleotide sequence corresponding to the 31,321,210th position to the 31,321,235th position in a human genome sequence (Reference sequence: hg19).

The length of a PCR product obtained by using the primer set is estimated as about 4,600 bases (bp).

In Table 1, SEQ ID NOS: 6 to 8 represent a set of PCR primers specifically amplifying a HLA-C gene, which is an α chain of MHC class I. These primers of the set are nucleotide sequences located at positions, which correspond to the upstream and downstream of all regions of a HLA-C gene (including promoter, exons and introns) and sandwich the all regions, in the human genome sequence (Reference sequence: hg19).

SEQ ID NO: 6 or 7 has a complementary nucleotide sequence to a nucleotide sequence corresponding to the 31,240,868th position to the 31,240,896th position in a human genome sequence (Reference sequence: hg19).

SEQ ID NO: 8 has a nucleotide sequence corresponding to the 31,236,075st position to the 31,236,114th position in a human genome sequence (Reference sequence: hg19).

The length of a PCR product obtained by using these primer sets is estimated as about 4,800 bases (bp).

TABLE 1

| HLA-class I gene | Name of primer | Length of primer (mer) | Primer sequence (5'-3') | SEQ ID NO: | Estimated length of PCR product based on the reference sequence (hg19) (bp) |
|---|---|---|---|---|---|
| HLA-A | A_F1.4 | 32 | CAGAAACTCAGAGCTAAGGAATGATGGCAAAT | SEQ ID NO: 1 | 5,472 |
|  | A_F2.4 | 32 | CAGAAACTCAGAGCTATGGAATGATGGTAAAT | SEQ ID NO: 2 |  |
|  | A_R1.2 | 30 | GCATATAACCATCATCGTGTCCCAAGGTTC | SEQ ID NO: 3 |  |
| HLA-B | B_F1.4 | 29 | GGTTCCCGGTTGCAATAGACAGTAACAAA | SEQ ID NO: 4 | 4,615 |
|  | B_R1.2 | 26 | ACGGGTCCAATTTCACAGACAAATGT | SEQ ID NO: 5 |  |
| HLA-C | C_F1.4 | 29 | ACACTGCTTAGATGTGCATAGTTCACGAA | SEQ ID NO: 6 | 4,822 |
|  | C_F2.4 | 29 | ACACTGCTTAGATGTGCATAGTTCCGGAA | SEQ ID NO: 7 |  |
|  | C_R1.16 | 40 | GAACAATTCTAGACTATGGACCCAATTTTACAAACAAATA | SEQ ID NO: 8 |  |

In Table 2, SEQ ID NOS: 9 and 10 represent a set of PCR primers specifically amplifying HLA-DR2 (DR15) and/or HLA-DR2 (DR16) subtype gene of a HLA-DRB1 gene, which is a β chain of MHC class II. These primers of the set are nucleotide sequences located at positions, which correspond to the upstream and downstream of exon 2 to a 3' untranslated region of a HLA-DRB1 gene and sandwich the region, in the human genome sequence (Reference sequence: hg19).

SEQ ID NO: 10 has a nucleotide sequence corresponding to the 32,546,609th position to the 32,546,629th position in a human genome sequence (Reference sequence: hg19).

SEQ ID NO: 9 has a complementary nucleotide sequence to a nucleotide sequence corresponding to the 32,552,130th position to the 32,552,153rd position in a human genome sequence (Reference sequence: hg19).

The length of a PCR product obtained by using the primer set is estimated as about 5,600 bases (bp).

In Table 2, SEQ ID NOS: 11 and 12 represent a set of PCR primers of specifically amplifying HLA-DR3, HLA-DR5 (DR11), HLA-DR5 (DR12), HLA-DR6 (DR13), HLA-DR6 (DR14) and/or a HLA-DR8 subtype gene of a HLA-DRB1 gene, which is a β chain of MHC class II. These primers of the set are nucleotide sequences located at positions, which correspond to the upstream and downstream of exon 2 to a 3' untranslated region of a HLA-DRB1 gene and sandwich the region, in the human genome sequence (Reference sequence: hg19).

SEQ ID NO: 12 has a nucleotide sequence corresponding to the 32,546,608th position to the 32,546,629th position in a human genome sequence (Reference sequence: hg19).

SEQ ID NO: 11 has a complementary nucleotide sequence to a nucleotide sequence corresponding to the 32,552,137th position to the 32,552,162nd position in a human genome sequence (Reference sequence: hg19).

The length of a PCR product obtained by using the primer set is estimated as about 5,600 bases (bp).

In Table 2, SEQ ID NOS: 13 to 15 represent a set of PCR primers specifically amplifying a HLA-DRB3 gene, which is a β chain of MHC class II. These primers of the set are nucleotide sequences located at positions, which correspond to the upstream and downstream of exon 2 to a 3' untranslated region of a HLA-DRB3 gene and sandwich the region, in the human genome sequence (Reference sequence: 6_cox_hap2).

SEQ ID NO: 13 or 14 has a complementary nucleotide sequence to a nucleotide sequence corresponding to the 3,939,356th position to the 3,939,379th position in a human genome sequence (Reference sequence: 6_cox_hap2).

SEQ ID NO: 15 has a nucleotide sequence corresponding to the 3,934,187th position to the 3,934,207th position in a human genome sequence (Reference sequence: 6_cox_hap2).

The length of a PCR product obtained by using these primer sets is estimated as about 5,200 bases (bp).

In Table 2, SEQ ID NOS: 16 and 17 represent a set of PCR primers specifically amplifying a HLA-DRB4 gene, which is a β chain of MHC class II. These primers of the set are nucleotide sequences located at positions, which correspond to the upstream and downstream of exon 2 to a 3' untranslated region of a HLA-DRB4 gene and sandwich the region, in the human genome sequence (Reference sequence: chr6_mamn_hap4).

SEQ ID NO: 16 has a complementary nucleotide sequence to a nucleotide sequence corresponding to the 3,851,270th position to the 3,851,293rd position in a human genome sequence (Reference sequence: chr6_mann_hap4).

SEQ ID NO: 17 has a nucleotide sequence corresponding to the 3,846,108th position to the 3,846,128th position in a human genome sequence (Reference sequence: chr6_mann_hap4).

The length of a PCR product obtained by using the primer set is estimated as about 5,200 bases (bp).

In Table 2, SEQ ID NOS: 18 and 19 represent a set of PCR primers specifically amplifying a HLA-DRB5 gene, which is a β chain of MHC class II. These primers of the set are nucleotide sequences located at positions, which correspond to the upstream and downstream of exon 2 to a 3' untranslated region of a HLA-DRB5 gene and sandwich the region, in the human genome sequence (Reference sequence: hg19).

SEQ ID NO: 18 has a complementary nucleotide sequence to a nucleotide sequence corresponding to the 32,489,933rd position to the 32,489,956th position in a human genome sequence (Reference sequence: hg19).

SEQ ID NO: 19 has a nucleotide sequence corresponding to the 32,485,256th position to the 32,485,276th position in a human genome sequence (Reference sequence: hg19).

The length of a PCR product obtained by using the primer set is estimated as about 4,700 bases (bp).

sandwich the all regions, in the human genome sequence (Reference sequence: hg19).

TABLE 2

| HLA-class II gene | Name of primer | Length of primer (mer) | Primer sequence (5'-3') | SEQ ID NO: | Estimated length of PCR product based on the reference sequence (bp) |
|---|---|---|---|---|---|
| HLA-DR2 (DR15) | DRB1-E2-2-F2 | 24 | CGTTTCCTGTGGCAGCCTAAGAGG | SEQ ID NO: 9 | 5,545 (reference sequence: hg19) |
|  | DRB1-E2-12-R | 21 | ATGCACGGGAGGCCATACGGT | SEQ ID NO: 10 |  |
| HLA-DR2 (DR16) | DRB1-E2-2-F2 | 24 | CGTTTCCTGTGGCAGCCTAAGAGG | SEQ ID NO: 9 | 5,545 (reference sequence: hg19) |
|  | DRB1-E2-12-R | 21 | ATGCACGGGAGGCCATACGGT | SEQ ID NO: 10 |  |
| HLA-DR3 | DRB1-E2-3568-F2 | 26 | CCCACAGCACGTTTCTTGGAGTACTC | SEQ ID NO: 11 | 5,555 (reference sequence: hg19) |
|  | DRB1-E2-3568-R2 | 22 | GATGCACAGGAGGCCATAGGGT | SEQ ID NO: 12 |  |
| HLA-DR5 (DR11) | DRB1-E2-3568-F2 | 26 | CCCACAGCACGTTTCTTGGAGTACTC | SEQ ID NO: 11 | 5,555 (reference sequence: hg19) |
|  | DRB1-E2-3568-R2 | 22 | GATGCACAGGAGGCCATAGGGT | SEQ ID NO: 12 |  |
| HLA-DR5 (DR12) | DRB1-E2-3568-F2 | 26 | CCCACAGCACGTTTCTTGGAGTACTC | SEQ ID NO: 11 | 5,555 (reference sequence: hg19) |
|  | DRB1-E2-3568-R2 | 22 | GATGCACAGGAGGCCATAGGGT | SEQ ID NO: 12 |  |
| HLA-DR6 (DR13) | DRB1-E2-3568-F2 | 26 | CCCACAGCACGTTTCTTGGAGTACTC | SEQ ID NO: 11 | 5,555 (reference sequence: hg19) |
|  | DRB1-E2-3568-R2 | 22 | GATGCACAGGAGGCCATAGGGT | SEQ ID NO: 12 |  |
| HLA-DR6 (DR14) | DRB1-E2-3568-F2 | 26 | CCCACAGCACGTTTCTTGGAGTACTC | SEQ ID NO: 11 | 5,555 (reference sequence: hg19) |
|  | DRB1-E2-3568-R2 | 22 | GATGCACAGGAGGCCATAGGGT | SEQ ID NO: 12 |  |
| HLA-DR8 | DRB1-E2-3568-F2 | 26 | CCCACAGCACGTTTCTTGGAGTACTC | SEQ ID NO: 11 | 5,555 (reference sequence: hg19) |
|  | DRB1-E2-3568-R2 | 22 | GATGCACAGGAGGCCATAGGGT | SEQ ID 12 |  |
| HLA-DRB3 | DRB3-E2-F1 | 24 | CGCAGCACGTTTCTTGGAGCTGCG | SEQ ID NO: 13 | 5,193 (reference sequence: 6_cox_hap2) |
|  | DRB3-E2-F2 | 24 | CGCAGCACGTTTCTTGGAGCTGCT | SEQ ID NO: 14 |  |
|  | DRB3-E2-R1 | 21 | ATGCACAGGAGGCCATAGGGT | SEQ ID NO: 15 |  |
| HLA-DRB4 | DRB4-E2-F1 | 24 | CACAGCACGTTTCTTGGAGCAGGC | SEQ ID NO: 16 | 5,186 (reference sequence: 6_mann_hap2) |
|  | DRB4-E2-R1 | 21 | ATGCATGGGAGGCAGGACAGT | SEQ ID NO: 17 |  |
| HLA-DRB5 | DRB5-E2-F1 | 24 | CACAGCACGTTTCTTGCAGCAGGA | SEQ ID NO: 18 | 4,701 (reference sequence: hg19) |
|  | DRB5-E2-R1 | 21 | ATGCATGGGAGGCCGTAGGGT | SEQ ID NO: 19 |  |

In Table 3, SEQ ID NOS: 20 and 21 represent a set of PCR primers specifically amplifying a HLA-DQA1 gene, which is a α chain of MHC class II. These primers of the set are nucleotide sequences located at positions, which correspond to the upstream and downstream of all regions (including promoter, exons and introns) of a HLA-DQA1 gene and sandwich the all regions, in the human genome sequence (Reference sequence: hg19).

SEQ ID NO: 20 has a nucleotide sequence corresponding to the 32,604,465th position to the 32,604,488th position in a human genome sequence (Reference sequence: hg19).

SEQ ID NO: 21 has a complementary nucleotide sequence to a nucleotide sequence corresponding to the 32,611,936th position to the 32,611,960th position in a human genome sequence (Reference sequence: hg19).

The length of a PCR product obtained by using the primer set is estimated as about 7,500 bases (bp).

In Table 3, SEQ ID NOS: 22 to 26 represent a set of PCR primers specifically amplifying a HLA-DQB1 gene, which is a β chain of MHC class II. These primers of the set are nucleotide sequences located at positions, which correspond to the upstream and downstream of all regions (including promoter, exons and introns) of a HLA-DQB1 gene and sandwich the all regions, in the human genome sequence (Reference sequence: hg19).

SEQ ID NO: 22 has a nucleotide sequence corresponding to the 32,627,406th position to the 32,627,433rd position in a human genome sequence (Reference sequence: hg19).

SEQ ID NO: 23 or 25 has a nucleotide sequence corresponding to the 32,635,612nd position to the 32,635,643rd position in a human genome sequence (Reference sequence: hg19).

SEQ ID NO: 24 or 26 has a complementary nucleotide sequence to a nucleotide sequence corresponding to the 32,635,612nd position to the 32,635,640th position in a human genome sequence (Reference sequence: hg19).

The length of a PCR product obtained by using these primer sets is estimated as about 8,200 bases (bp).

In Table 3, SEQ ID NOS: 27 to 29 represent a set of PCR primers specifically amplifying a HLA-DPA1 gene, which is a α chain of MHC class II. These primers of the set are nucleotide sequences located at positions, which correspond to the upstream and downstream of all regions (including promoter, exons and introns) of a HLA-DPA1 gene and sandwich the all regions, in the human genome sequence (Reference sequence: hg19).

SEQ ID NO: 27 has a complementary nucleotide sequence to a nucleotide sequence corresponding to the 33,041,573rd position to the 33,041,600th position in a human genome sequence (Reference sequence: hg19).

SEQ ID NO: 28 has a complementary nucleotide sequence to a nucleotide sequence corresponding to the 33,041,573rd position to the 33,041,598th position in a human genome sequence (Reference sequence: hg19).

SEQ ID NO: 29 has a nucleotide sequence corresponding to the 33,031,885th position to the 33,031,912nd position in a human genome sequence (Reference sequence: hg19).

The length of a PCR product obtained by using these primer sets is estimated as about 9,700 bases (bp).

In Table 3, SEQ ID NOS: 30 and 31 represent a set of PCR primers specifically amplifying a HLA-DPB1 gene, which is a β chain of MHC class II. These primers of the set are nucleotide sequences located at positions, which correspond to the upstream and downstream of exon 2 to a 3' untranslated region of a HLA-DPB1 gene and sandwich the region, in the human genome sequence (Reference sequence: hg19).

SEQ ID NO: 30 has a nucleotide sequence corresponding to the 33,048,182nd position to the 33,048,207th position in a human genome sequence (Reference sequence: hg19).

SEQ ID NO: 31 has a complementary nucleotide sequence to a nucleotide sequence corresponding to the 33,055,428th position to the 33,055,453rd position in a human genome sequence (Reference sequence: hg19).

The length of a PCR product obtained by using these primer sets is estimated as about 7,300 bases (bp).

TABLE 3

| HLA-class II gene | Name of primer | Length of primer (mer) | Primer sequence (5'-3') | SEQ ID NO: | Estimated length of PCR product based on the reference sequence (hg19) (bp) |
|---|---|---|---|---|---|
| HLA-DQA1 | DQA1-F2.2 | 24 | GACTGCCAGGGAGGGAAATCRACT | SEQ ID NO: 20 | 7,496 |
|  | DQA1-R2.2 | 25 | GCGAATCCAGTGGAGGACACAGCAC | SEQ ID NO: 21 |  |
| HLA-DQB1 | DQB1-F6.3 | 28 | CAAACCAGAAGAGAGGCTGGGATATTCT | SEQ ID NO: 22 | 8,238 |
|  | DQB1-R3.1.2 | 32 | AACCATTAGTATTGCCCCTAGTCACTGTCAAG | SEQ ID NO: 23 |  |
|  | DQB1-R3.2.2 | 29 | CATTAGTACTGCCCCTAGTCACTGCCAAG | SEQ ID NO: 24 |  |
|  | DQB1-R3.3.2 | 32 | AACCATTAGTACTGTCCCTAGTCACTGCCAAG | SEQ ID NO: 25 |  |
|  | DQB1-R3.4.2 | 29 | CATTAGTACTGCCCCTAGTCACTGGCAAG | SEQ ID NO: 26 |  |
| HLA-DPA1 | DPA1-F1.1.2 | 28 | GGAGCTCTCTTAACCACGCTGGTACCTA | SEQ ID NO: 27 | 9,716 |
|  | DPA1-F1.2.2 | 26 | AGCTCTCTTGACCACGCTGGTACCTA | SEQ ID NO: 28 |  |
|  | DPA1-R1.1.2 | 28 | CCATTGGCCTCTTGGCTATACCTCTTTT | SEQ ID NO: 29 |  |
| HLA-DPB1 | DPB1-F2 | 26 | CTCAGTGCTCGCCCCTCCCTAGTGAT | SEQ ID NO: 30 | 7,272 |
|  | DPB1-R2 | 26 | GCACAGTAGCTTTCGGGAATTGACCA | SEQ ID NO: 31 |  |

These primers can be prepared by a method routinely used in this field. Furthermore, the sets of primers described in Table 1 to Table 3 are the most preferable examples. In the method of the present invention, any set of primers can be used as long as the set of primers is a set of a sense primer and a anti-sense primer capable of annealing to the positions, which correspond to the upstream and downstream of all regions of each HLA gene and sandwich the all regions.

Further, in the present specification, even if primers correspond to the same region within the reference sequence, a separate sequence ID number is assigned to each primer as long as they differ in the nucleotides. The difference in the nucleotide is due to a polymorphism.

(2) Step of PCR Amplification

In the method of the present invention, a test sample (DNA) is amplified by PCR using the sets of primers prepared in the above step (1).

The PCR amplification reaction is performed in accordance with a general protocol and more specifically, as follows.

1. DNA is extracted from a test sample depending upon the form of the sample.

2. The DNA extracted is quantified and the concentrations of primers are appropriately set to prepare the reaction solution.

3. Reaction conditions are set and a PCR is performed. For example:
Thermal denaturation step (usually 92 to 98° C.)
Annealing step (usually 55 to 72° C.)
Extension step (usually 65 to 80° C.)

In the method of the present invention, the temperature of the annealing step and the extension step is set preferably at about 65 to 70° C., more preferably at 65 to 68° C. Owing to the annealing and extension at about 65 to 70° C., HLA alleles can be produced at the equivalent ratio (uniformly).

4. The obtained PCR product is purified and subjected to the following nucleotide sequencing step.

Owing to use of the sets of primers according to the present invention, a plurality of different genes can be simultaneously amplified under the same conditions by a single reaction in a single tube.

The enzyme (DNA polymerase) used in the present invention is not particularly limited and may be commercial products. Examples include PRIMESTAR® GXL long range DNA polymerase, TKS GFLEX® long range DNA polymerase, or TAKARA LA TAQ® long range DNA polymerase (each manufactured by TaKaRA BIO INC.); LONG PCR ENZYME MIX DNA polymerase blend(manufactured by Thermo Fisher Scientific) and the like.

(3) Step of Nucleotide Sequencing

Next, the nucleotide sequence of the PCR product (amplified DNA) produced in the above step (2) is determined. The step is preferably performed by a technique called high throughput sequencing (or ultrahigh sequencing, a massive parallel sequencing). With respect to the high throughput sequencing, see, for example, "Experimental Medicine", Vol. 27, No. 1, 2009 (Yodo-sha).

Herein, a sequencing method which is employed in a 454 GS sequencing system of Roche will be described below. Alternatively, sequencing may be also performed by the genome sequencer ION TORRENT PGM™ sequencing system by Life Technologies Corporation; or MISEQ® sequencing system by Illumina, Inc.

1. The PCR product obtained in the above step (2) is broken up by a nebulizer into fragments of about 500 bases.
2. To an end of each of the DNA fragments, a DNA adaptor is attached.
3. DNA fragments attached with a DNA adaptor are dissociated into single stranded DNA fragments, which are allowed to bind to beads via the adaptor. The obtained beads are encompassed and taken in a water-in-oil emulsion (a micro-reactor environment containing a single DNA fragment bound to a single bead is formed).
4. Emulsion PCR is performed to form copies of each DNA fragment on a bead (Each DNA fragment is clonally amplified in each micro reactor. In this manner, many fragments can be simultaneously and in parallel amplified without competition with other sequences). Subsequently, the emulsion is destroyed and beads having amplified DNA fragments are collected.
5. The beads are concentrated and loaded in a pico-titer plate (a single well has a size enough to place a single bead).
6. Pyrophosphoric acid produced by a polymerase during an enzymatic reaction is detected with respect to each bead by a fluorescent reaction of luciferase. Based on the intensity and the pattern of fluorescence thus emitted, the nucleotide sequence of DNA is determined. Four types of nucleic acids (A, C, G, T) are added in a predetermined order. The chemiluminescence pattern in accordance with the nucleic acid added is recorded. Based on the intensity of signal and positional data in combination, the nucleotide sequence is determined.

(4) Step of DNA Typing

Subsequently, after the sff file obtained in the above step (3) is classified depending on MID tags, it is compared with data of known HLA alleles within the nucleotide sequencing database. In this manner, the allele type (8 digits) contained in the test sample is determined at the field 4 level.

In the method of the present invention, typical sets of primers are listed in Table 1 to Table 3 (described above). The present invention is characterized in that primers are designed so as to correspond to the upstream and downstream of all regions of each of the genes of HLA class I and HLA class II and sandwich the all regions and the sequence of the DNA amplified corresponding to almost all regions is determined. In this manner, phase ambiguity (uncertainty) is eliminated and information on a null allele can be obtained.

According to the present invention, since sets of primers for HLA genes are designed so as to anneal at the same temperature during PCR, PCR can be simultaneously performed for a plurality of genes in a single PCR apparatus.

Additionally, owing to the primer sets according to the present invention, a multiplex PCR method wherein a plurality of HLA genes are simultaneously PCR amplified in a single tube can be performed.

Furthermore, it has been confirmed that sets of primers and enzymes used in the present invention can be applied to a high-speed PCR apparatus. Thus, PCR can be performed more rapidly and accurately than before.

EXAMPLES

The present invention will be more specifically described by way of Examples below; however, the present invention is not limited to these Examples.

Test Example 1

[Purpose]

The purpose of this test example is to identify the PCR enzymes suitable for the method according to the present invention.

[Method]

A PCR was carried out using sets of primers specifically amplifying a promoter region to exon 2 of HLA-DRB1 (see, Non Patent Document 2) and two genome DNA samples as a template. The genome DNA samples have been prospectively extracted and each contains DR9 and DR15 as a heterozygote.

Since the length of the PCR product for DR9 is 11.2 kb and the length of the PCR product for DR15 is 6.1 kb, it is easy to confirm that both HLA alleles are amplified equally. Since the PCR product of DR9 is the longest out of those of HLA genes used in the present invention, it can be considered to be capable of amplifying HLA genes other than DR9 in the same manner if the PCR product of DR9 is obtained. From these, the genome DNA having DR9 and DR15 as a heterozygote was selected as a sample.

(1) Twenty-three commercially available long range PCR enzymes listed in Table 4 were used in the PCR. More specifically, to 50 ng of a genomic DNA solution, 1.5 to 3 µL (4 pmol/µL) of PCR primers and a PCR buffer, a dNTP solution and a long range PCR enzyme depending on the protocol for each enzyme were added. The whole amount of the reaction solution was adjusted to be 20 µL with sterilized water.

(2) After kept at 94° C. for 2 minutes, the reaction solution was subjected to a step consisting of a reaction at 98° C. for 10 seconds and a reaction at 68° C. for 5 minutes. This step was repeated 30 times. Note that, for the PCR amplification, GENEAMP® PCR System 9700 high throughput sequencing system (Life Technologies Corporation) was used. After the PCR, the amplification states of PCR products were checked by agarose gel electrophoresis. The electrophoretic patterns were shown in FIG. 6.

[Results and Discussion]

Figure 6:
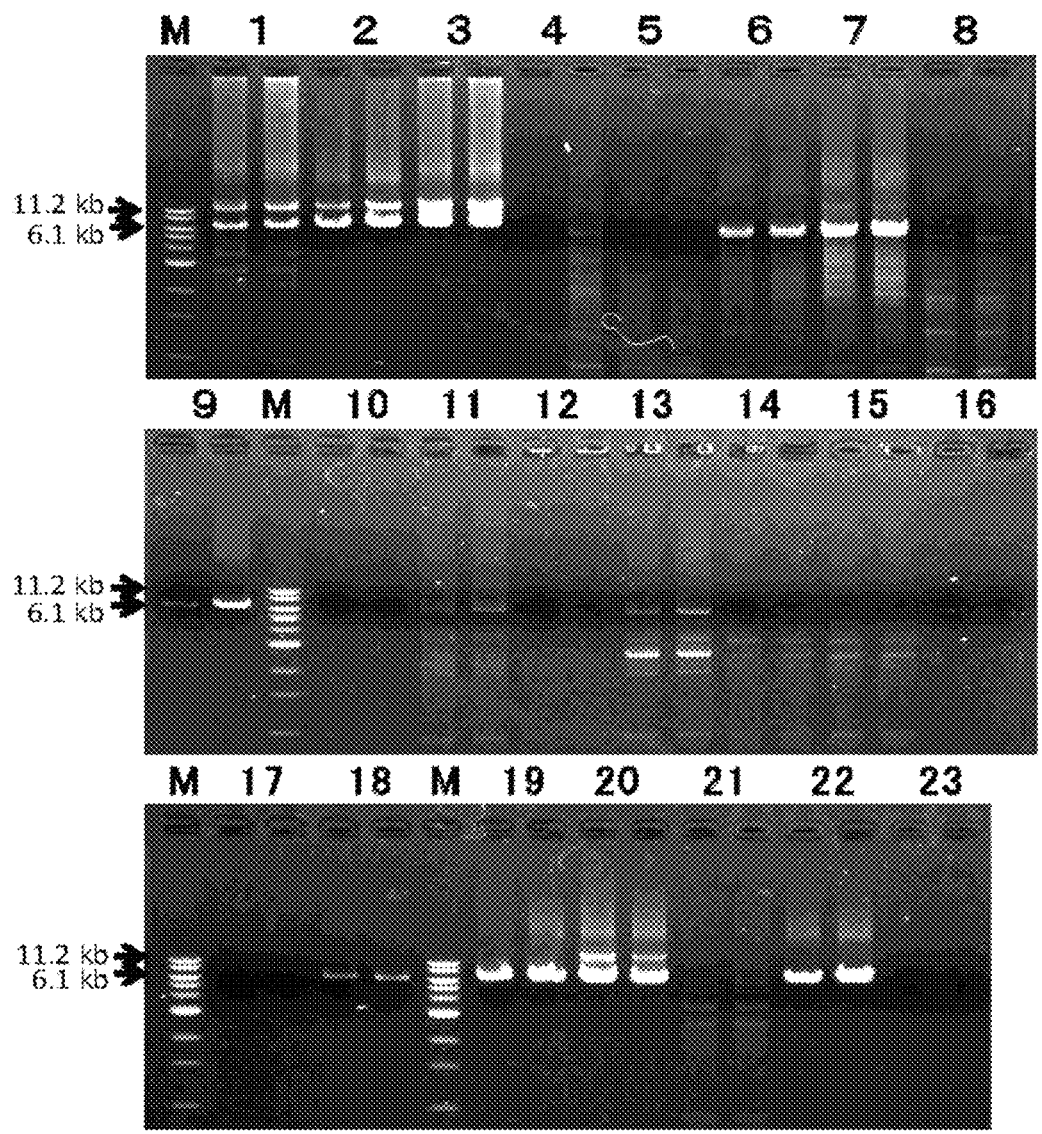
FIG. 6 An agarose gel electrophoretic pattern showing amplification states of HLA-DRB1 genes amplified in Test Example 1.

After the PCR and the agarose gel electrophoresis using the PCR products according to the standard protocol, PCR products having the desired molecular weight from both HLA alleles ware obtained for each sample when four kinds of enzyme: PRIMESTAR® GXL long range DNA polymerase (TaKaRa), TAKARA LA TAQ® long range DNA polymerase (TaKaRa), TKS GFLEX® long range DNA polymerase (TaKaRa), and LONG PCR ENZYME MIX DNA polymerase blend (Thermo SCIENTIFIC) were used (FIG. 6).

Additionally, from the results of the Test Example 1, it was demonstrated that the three kinds of enzyme: PRIMESTAR® GXL long range DNA polymerase (TaKaRa), TAKARA LA TAQ® long range DNA polymerase (TaKaRa), and TKS GFLEX® long range DNA polymerase (TaKaRa) among the four kinds of enzyme can amplify each allele from HLA genes almost equally by PCR. Therefore, the three kinds of enzyme were confirmed to be especially suitable for the method according to the present invention.

1 to 3 µL of PCR primers (4 pmol/µL) for each and 0.4 µL of PRIMESTAR® GXL DNA polymerase were added. The whole amount of the reaction solution was adjusted to be 20 µL with sterilized water.

(2) After kept at 94° C. for 2 minutes, the reaction solution was subjected to a step consisting of a reaction at 98° C. for 10 seconds and a reaction at 70° C. for 5 minutes. This step was repeated 30 times. Note that, for the PCR amplification, GENEAMP® PCR System 9700 high throughput sequencing system (Life Technologies Corporation) was used. After the PCR, the amplification states of PCR products were checked by agarose gel electrophoresis. The electrophoretic patterns were shown in FIG. 7.

[Results and Discussion]

PCR conditions using PRIMESTAR® GXL long range DNA polymerase (TaKaRa) were studied and agarose gel electrophoresis of the resultant PCR products was performed. As a result, it was found that a single PCR amplified product having a desired molecular weight was obtained for each of HLA class I and HLA class II genes (FIG. 7).

Example 2

[Purpose]

The purpose of this example is to check the amplification states of PCR products of HLA genes using TKS GFLEX® long range DNA polymerase (TaKaRa).

TABLE 4

| Enzyme No.* | Manufacturer | Product name |
| --- | --- | --- |
| 1 | TaKaRa | PRIMESTAR (R) GXL long range DNA polymerase |
| 2 | TaKaRa | TAKARA LA TAQ (R) long range DNA polymerase |
| 3 | TaKaRa | TKS GFLEX (R) long range DNA polymerase |
| 4 | TaKaRa | PRIMESTAR (R) MAX DNA polymerase |
| 5 | TaKaRa | PRIMESTAR (R) HS DNA polymerase |
| 6 | TOYOBO | KOD FX (TM) DNA polymerase |
| 7 | TOYOBO | KOD FX NEO (TM) DNA polymerase |
| 8 | TOYOBO | KOD-PLUS-NEO (TM) DNA polymerase |
| 9 | Roche Applied Science | EXPAND (TM) 20 KB PLUS PCR system, dNTPack |
| 10 | Roche Applied Science | EXPAND (TM) LONG RANGE PCR system, dNTPack |
| 11 | Agilent Technologies | PFUULTRA II FUSION HS DNA polymerase |
| 12 | Agilent Technologies | PFUTURBO DNA polymerase |
| 13 | NEW ENGLAND BioLabs | Q5 (R) HOT START HIGH-FIDELITY 2X master mix |
| 14 | NEW ENGLAND BioLabs | IPROOF (TM) HS master mix |
| 15 | NEW ENGLAND BioLabs | IPROOF (TM) GC master mix |
| 16 | SIGMA-ALDRICH | ACCUTAQ (TM) LA DNA polymerase |
| 17 | SIGMA-ALDRICH | REDACCUTAQ (R) LA DNA polymerase |
| 18 | SIGMA-ALDRICH | JUMPSTART (TM) ACCUTAQ (TM) LA DNA polymerase |
| 19 | SIGMA-ALDRICH | JUMPSTART (TM) REDACCUTAQ (R) LA DNA polymerase |
| 20 | Thermo SCIENTIFIC | LONG PCR ENZYME MIX DNA polymerase blend |
| 21 | Thermo SCIENTIFIC | HIGH FIDELITY PCR master mix |
| 22 | Promega | GOTAQ (R) LONG PCR master mix |
| 23 | LifeTechnologies | PLATINUM (TM) PFX long range DNA Polymerase |

*The enzyme number corresponds to the lane number in FIG. 6.

Example 1

[Purpose]

The purpose of this example is to check the amplification states of PCR products of HLA genes using PRIMESTAR® GXL long range DNA polymerase (TaKaRa).

[Method]

Using PRIMESTAR® GXL long range DNA polymerase (TaKaRa), genomic DNA already extracted as a template and primer sets specific to individual HLA class I and HLA class II genes (see Tables 1 to 3: SEQ ID NOS: 1 to 31), a PCR was carried out. The procedure is more specifically as follows.

(1) To 50 ng of a genomic DNA solution, 4 µL of 5×PRIMESTAR® GXL buffer, 1.6 µL of a dNTP solution,

[Method]

Using TKS GFLEX® long range DNA polymerase (TaKaRa), genomic DNA already extracted as a template and primer sets specific to individual HLA class I and HLA class II genes (see Tables 1 to 3: SEQ ID NOS: 1 to 31), a PCR was carried out. The procedure is more specifically as follows.

(1) To 50 ng of a genomic DNA solution, 10 µL of 2×GFLEX PCR buffer, 1 to 3 µL of PCR primers (4 pmol/µL) and 0.2 µL of TKS GFLEX® long range DNA polymerase were added. The whole amount of the reaction solution was adjusted to be 20 µL with sterilized water.

(2) After kept at 94° C. for 2 minutes, the reaction solution was subjected to a step consisting of a reaction at 98° C. for 10 seconds and a reaction at 68° C. for 5 minutes. This step was repeated 10 times. Subsequently, the reaction solution was subjected to a step consisting of a reaction at 98° C. for 10 seconds and a reaction at 65° C. for 5 minutes. This step was repeated 20 times. Note that, for the PCR amplification, GENEAMP® PCR System 9700 high throughput sequencing system (Life Technologies Corporation) was used. After the PCR, the amplification states of PCR products were checked by agarose gel electrophoresis. The electrophoretic patterns were shown in FIG. 8.

[Results and Discussion]

PCR conditions using TKS GFLEX® long range DNA polymerase (TaKaRa) were studied and agarose gel electrophoresis of the resultant PCR products was performed. As a result, it was found that a single PCR amplified product having a desired molecular weight was obtained for each of HLA class I and HLA class II genes (FIG. 8).

As compared with the results of Comparative Example 1, each HLA gene could be amplified equally and uniformly when TKS GFLEX® long range DNA polymerase (TaKaRa) was used.

Example 3

[Purpose]

The purpose of this example is to compare amplification states of PCR products between the general PCR cycler, GENEAMP® PCR System 9700 high throughput sequencing system (Life Technologies Corporation) and the PCR cycler specified for rapid PCR, PCR Thermal Cycler Fast PCR cycler (TaKaRa), and study time required for PCR.

[Method]

Using TKS GFLEX® long range DNA polymerase (TaKaRa), genomic DNA already extracted as a template and primer sets specific to individual HLA class I and HLA class II genes (see Tables 1 to 3: SEQ ID NOS: 1 to 31), a PCR was carried out. The procedure is more specifically as follows.

(1) To 50 ng of a genomic DNA solution, 10 μL of 2×GFLEX PCR buffer, 1 to 3 μL of PCR primers (4 pmol/μL) and 0.2 μL of TKS GFLEX® long range DNA polymerase were added. The whole amount of the reaction solution was adjusted to be 20 μL with sterilized water.

(2) After kept at 94° C. for 2 minutes, the reaction solution was subjected to a step consisting of a reaction at 98° C. for 10 seconds and a reaction at 68° C. for 5 minutes. This step was repeated 10 times. Subsequently, the reaction solution was subjected to a step consisting of a reaction at 98° C. for 10 seconds and a reaction at 65° C. for 5 minutes. This step was repeated 20 times. Note that, for the PCR amplification, GENEAMP® PCR System 9700 high throughput sequencing system (Life Technologies Corporation) and PCR Thermal Cycler Fast PCR cycler (TaKaRa) were used. After the PCR, the amplification states of PCR products were checked by agarose gel electrophoresis. The electrophoretic patterns were shown in FIG. 9.

[Results and Discussion]

The amplification states of PCR products obtained using GENEAMP® PCR System 9700 high throughput sequencing system (Life Technologies Corporation) were substantially the same as the amplification states of PCR products obtained using PCR Thermal Cycler Fast PCR cycler (TaKaRa), and a single PCR amplified product having a desired molecular weight was obtained for each of HLA class I and HLA class II genes (FIG. 9).

While it took 3 hours 10 min for PCR using GENEAMP® PCR System 9700 high throughput sequencing system (Life Technologies Corporation), it took 2 hours 45 min for PCR using PCR Thermal Cycler Fast PCR cycler (TaKaRa).

Therefore, the method according to the present invention can be applied to a high-speed PCR apparatus such as PCR Thermal Cycler Fast PCR cycler (TaKaRa) and was confirmed to contribute to acceleration of PCR.

Example 4

[Purpose]

The purpose of this example is to check a reproducibility of PCR products obtained using GENEAMP® PCR System 9700 high throughput sequencing system (Life Technologies Corporation) and TKS GFLEX® long range DNA polymerase (TaKaRa), and to determine nucleotide sequences of PCR products from a plurality of DNA samples so as to demonstrate that PCR conditions set in the present invention are suitable for a super high resolution DNA typing method of HLA genes.

[Method]

1. Using TKS GFLEX® long range DNA polymerase (TaKaRa), genomic DNA already extracted from four specimens (Sample 1 to 4) as a template and primer sets specific to individual HLA class I and HLA class II genes (see Tables 1 to 3: SEQ ID NOS: 1 to 31), a PCR was carried out. Note that, the HLA type for each of the four specimens has been already revealed and the specimens include a combination of alleles, in which phase ambiguity was observed in a conventional DNA typing method. The procedure is more specifically as follows.

(1) To 50 ng of a genomic DNA solution, 10 μL of 2×GFLEX PCR buffer, 1 to 3 μL of PCR primers (4 pmol/μL) and 0.2 μL of TKS GLFEX® long range DNA polymerase were added. The whole amount of the reaction solution was adjusted to be 20 μL with sterilized water.

(2) After kept at 94° C. for 2 minutes, the reaction solution was subjected to a step consisting of a reaction at 98° C. for 10 seconds and a reaction at 68° C. for 5 minutes. This step was repeated 10 times. Subsequently, the reaction solution was subjected to a step consisting of a reaction at 98° C. for 10 seconds and a reaction at 65° C. for 5 minutes. This step was repeated 20 times. Note that, for the PCR amplification, GENEAMP® PCR System 9700 high throughput sequencing system (Life Technologies Corporation) was used. After the PCR, the amplification states of PCR products were checked by agarose gel electrophoresis. The electrophoretic patterns were shown in FIG. 10.

2. The nucleotide sequences of the PCR products were determined specifically as follows.

(1) A PCR product was purified by QIAQUICK™ PCR purification kit (QIAGEN) in accordance with the standard protocol.

(2) The concentration of the purified PCR product was measured by PICOGREEN™ dsDNA quantitation kit (Invitrogen) in accordance with the standard protocol.

(3) A solution of the purified PCR product, a concentration of which was adjusted to be 500 ng/100 μL, was subjected to construction of a rapid library, and then, emulsion PCR and sequencing by GENOME SEQUENCER (GS) JUNIOR DNA sequencer (Roche) were carried out in accordance with the standard protocol to obtain nucleotide sequences of 20,000 reads per sample.

(4) A search for homology between these nucleotide sequences and known nucleotide sequences of HLA alleles on an IMGT HLA database was performed to select candidate alleles.

(5) The sequences of the candidate alleles were used as a reference. Mapping was performed by GS REFERENCE MAPPER software (Roche) on condition that the reference matches the read perfectly. The mapping state was checked visually to identify an HLA allele.

[Results and Discussion]

Figure 10:
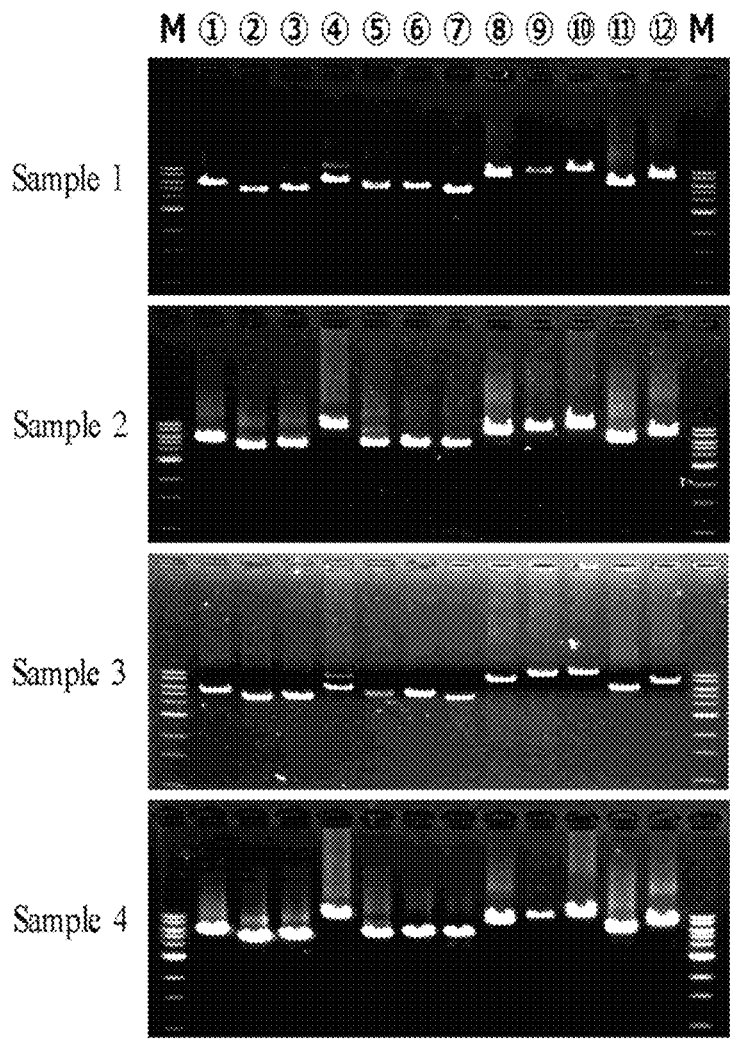
FIG. 10 An agarose gel electrophoretic pattern showing PCR states of HLA genes amplified in Example 4.

1. As seen in the agarose gel electrophoresis using PCR products, a single PCR amplified product having a desired molecular weight was obtained for each of HLA class I and HLA class II genes (FIG. 10). Furthermore, the nucleotide sequences of the PCR products were determined by the Sanger method. As a result, HLA alleles were obtained in consistent with known documents. It was confirmed herein again that the PCR system of the present invention can be used for HLA typing.

2. Using four specimens containing a combination of alleles, in which phase ambiguity is observed in a conventional DNA typing method, a PCR was performed. PCR products derived from the regions from a 5' untranslated region to exon 2 of HLA-A, HLA-B, HLA-C and HLA-DRB1 genes, the region from exon 2 to a 3' untranslated region of a HLA-DRB1 gene, the regions from a 5' untranslated region to exon 2 of HLA-DRB3/4/5, HLA-DQA1, HLA-DQB1, HLA-DPA1 and HLA-DPB1 genes, and the region from exon 2 to a 3' untranslated region of a HLA-DPB1 gene were subjected to HLA typing by GENOME SEQUENCER (GS) JUNIOR DNA sequencer (Roche). As a result, typing of whole gene regions of HLA-A, HLA-B, HLA-C, HLA-DRB1, HLA-DRB3/4/5 and HLA-DQB1 were successfully made. With respect to HLA-DQA1, HLA-DPA1 and HLA-DPB1, typing of an exon alone was successfully made. Furthermore, in each of the HLA-B, HLA-C, HLA-DRB1 and HLA-DQB1 genes, a novel allele was detected (Table 5). From this, it was demonstrated that the method of the present invention enables HLA typing at a 8-digit level without phase ambiguity; and that the method of the invention is an excellent tool for efficiently detecting a substitution, an insertion and a deletion of bases in a promoter and introns, which are causes of a null allele.

Example 5

[Purpose]

The purpose of this example is to determine the potentiality of a multiplex PCR method of HLA-A, HLA-B, HLA-C and HLA-DRB1 genes using TKS GFLEX® long range DNA polymerase (TaKaRa) and GENEAMP® PCR System 9700 high throughput sequencing system (Life Technologies Corporation).

[Method]

1. Using TKS GFLEX® long range DNA polymerase (TaKaRa), genomic DNA already extracted from four specimens (Sample 1 to 4) as a template and primer sets specific to individual HLA-A, HLA-B, HLA-C and HLA-DRB1 genes (see Patent Document 3 and Tables 1 and 2: SEQ ID NOS: 1 to 12), with mixed in a single tube, a PCR was carried out. Note that, the HLA type for each of the four specimens has been already revealed and the specimens include a combination of alleles, in which phase ambiguity was observed in a conventional DNA typing method. The procedure is more specifically as follows.

(1) To 50 ng of a genomic DNA solution, 10 μL of 2×GFLEX PCR buffer, 1 to 3 μL of PCR primers (4 pmol/μL) and 0.2 μL of TKS GFLEX® long range DNA polymerase were added. The whole amount of the reaction solution was adjusted to be 20 μL with sterilized water.

(2) After kept at 94° C. for 2 minutes, the reaction solution was subjected to a step consisting of a reaction at 98° C. for 10 seconds and a reaction at 68° C. for 5 minutes. This step was repeated 10 times. Subsequently, the reaction solution was subjected to a step consisting of a reaction at 98° C. for 10 seconds and a reaction at 65° C. for 5 minutes. This step was repeated 20 times. Note that, for the PCR amplification, GENEAMP® PCR System 9700 sequencing system (Life Technologies Corporation) was used. After the PCR, the amplification states of PCR products were checked by agarose gel electrophoresis. The electrophoretic patterns were shown in FIG. 11. Also, the length of PCR products was exactly determined by BIOANALYZER microfluidics platform (Agilent DNA12000 chips). The results were shown in FIG. 12.

TABLE 5

| DNA | HLA-A | | HLA-B | | HLA-C | |
|---|---|---|---|---|---|---|
| Sample ID | Allele 1 | Allele 2 | Allele 1 | Allele 2 | Allele 1 | Allele 2 |
| Sample 1 | A*02:06:01 | A*11:01:01 | B*40:02:01 | B*55:02:01:(02) | C*01:02:01 | C*03:03:01 |
| Sample 2 | A*26:01:01 | A*31:01:02 | B*15:01:01:01 | B*35:01:01:02 | C*03:04:01:02 | C*07:02:01:(04) |
| Sample 3 | A*24:02:01:01 | A*33:03:01 | B*44:03:01 | B*48:01:01 | C*08:03:01 | C*14:03 |
| Sample 4 | A*11:01:01 | A*31:01:02 | B*40:01:02 | B*51:01:01 | C*07:02:01:01 | C*15:02:01 |

| DNA | HLA-DRB1 | | HLA-DRB3/4/5 | | HLA-DQA1 | |
|---|---|---|---|---|---|---|
| Sample ID | Allele 1 | Allele 2 | Allele 1 | Allele 2 | Allele 1 | Allele 2 |
| Sample 1 | DRB1*09:01:02:(01) | DRB1*15:01:01:01/02/03 | DRB4*01:03:02:(01) | DRB5*01:01:01:(02) | DQA1*01:02:01 | DQA1*03:02 |
| Sample 2 | DRB1*09:01:02:(01) | DRB1*13:02:01:(02) | DRB3*03:01:01:(01) | DRB4*01:03:02:(01) | DQA1*01:02:01 | DQA1*03:02 |
| Sample 3 | DRB1*13:02:01:(02) | DRB1*16:02:01:(02) | DRB3*03:01:01:(01) | DRB5*02:02:(01):(01) | DQA1*01:02:01 | DQA1*01:02:02 |
| Sample 4 | DRB1*09:01:02:(01) | DRB1*12:01:01:(02) | DRB3*01:01:02:(03) | DRB4*01:03:02:(01) | DQA1*03:02 | — |

| DNA | HLA-DQB1 | | HLA-DPA1 | | HLA-DPB1 | |
|---|---|---|---|---|---|---|
| Sample ID | Allele 1 | Allele 2 | Allele 1 | Allele 2 | Allele 1 | Allele 2 |
| Sample 1 | DQB1*03:03:02:03 | DQB1*06:02:01 | DPA1*01:03:01 | — | DPB1*02:01:02 | DPB1*03:01:01 |
| Sample 2 | DQB1*03:03:02:02 | DQB1*06:04:01:(01) | DPA1*01:03:01 | — | DPB1*02:01:02 | DPB1*04:01:01 |
| Sample 3 | DQB1*05:02:01:(01) | DQB1*06:04:01:(01) | DPA1*01:03:01 | DPA1*02:02:02 | DPB1*04:01:01 | DPB1*05:01:01 |
| Sample 4 | DOB1*03:03:02:02 | — | DPA1*02:02:02 | — | DPB1*05:01:01 | — |

2. The nucleotide sequences of the PCR products were determined specifically as follows.

(1) A PCR product was purified by QIAQUICK™ PCR purification kit (QIAGEN) in accordance with the standard protocol.

(2) The concentration of the purified PCR product was measured by PICOGREEN™ dsDNA quantitation kit (Invitrogen) in accordance with the standard protocol.

(3) A solution of the purified PCR product, a concentration of which was adjusted to be 500 ng/100 μL, was subjected to construction of a rapid library, and then, emulsion PCR and sequencing by GENOME SEQUENCER (GS) JUNIOR DNA sequencer (Roche) were carried out in accordance with the standard protocol to obtain nucleotide sequences of 20,000 reads per sample.

(4) A search for homology between these nucleotide sequences and known nucleotide sequences of HLA alleles on an IMGT HLA database was performed to select candidate alleles.

(5) The sequences of the candidate alleles were used as a reference. Mapping was performed by GS REFERENCE MAPPER software (Roche) on condition that the reference matches the read perfectly. The mapping state was checked visually to identify an HLA allele.

[Results and Discussion]

Figure 11:
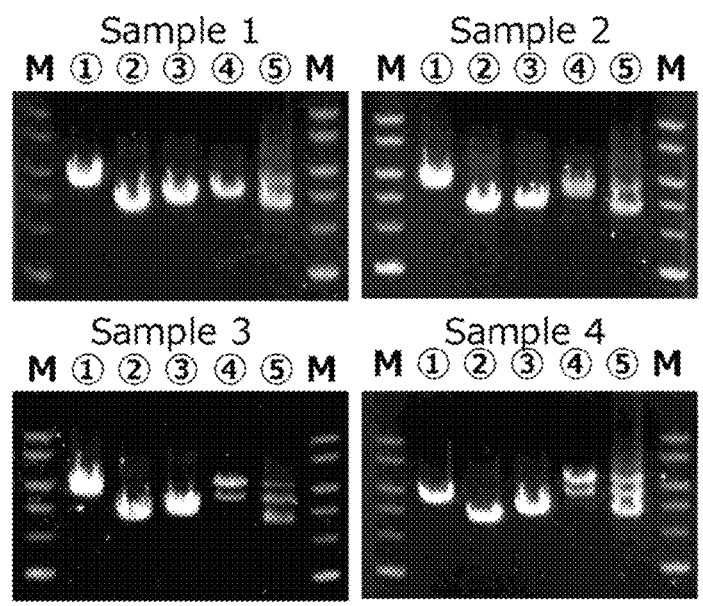
FIG. 11 An agarose gel electrophoretic pattern showing PCR states of HLA-A, HLA-B, HLA-C and HLA-DRB1 genes amplified in Example 5.
Figure 12:
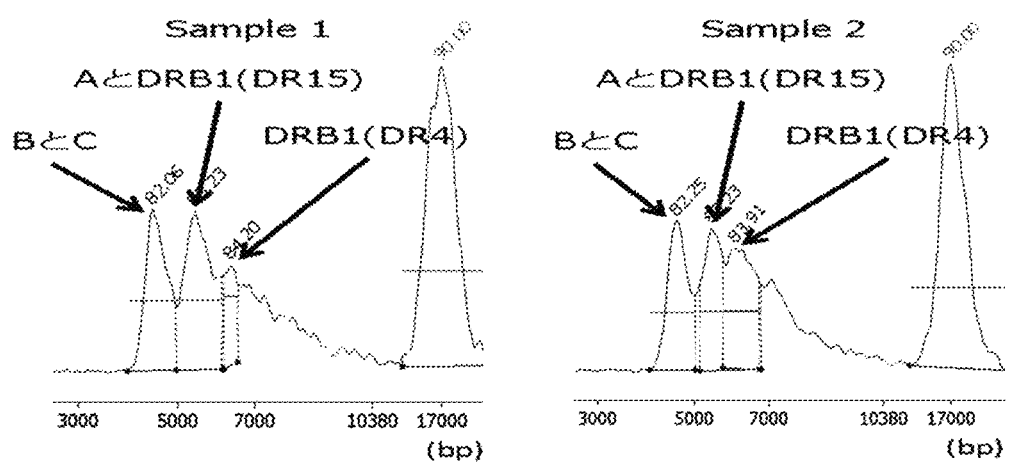
FIG. 12 Results regarding the lengths of multiplex PCR products of HLA-A, HLA-B, HLA-C and HLA-DRB1 genes amplified in Example 5 as measured by the bioanalyzer.

When HLA-A, HLA-B, HLA-C and HLA-DRB1 genes were amplified by PCR separately, as seen in the agarose gel electrophoresis using PCR products, a single PCR amplified product having a desired molecular weight was obtained (lanes 1 to 4 in FIG. 11). On the other hand, when primer sets of these genes were used by mixture for the PCR amplification, a plurality of bands predicted to represent PCR products from these genes were observed (lane 5 in FIG. 11). Also, the length of the PCR product was exactly determined by BIOANALYZER microfluidics platform (Agilent DNA12000 Kit). As a result, it was confirmed that the PCR product included products amplified from each of HLA-A, HLA-B, HLA-C and HLA-DRB1 genes (FIG. 12). Additionally, the PCR product was subjected to HLA typing by GENOME SEQUENCER (GS) JUNIOR DNA sequencer (Roche). The HLA alleles identified by the HLA typing were found to be consistent with the HLA alleles identified by Example 4. Therefore, the multiplex PCR method according to the present invention, when a high-speed PCR apparatus is used, was considered to be an excellent tool serving for accelerating and simplifying a complicated operation in clinical practice.

Comparative Example 1

[Purpose]

The purpose of this example is to confirm that the primer sets according to the present invention is suitable for a multiplex PCR amplification.

[Method]

PCR amplification using primer sets described in the Patent Document 2, which are specific to individual HLA-A, HLA-B, HLA-C and HLA-DRB1 genes, was performed under the same condition as Example 5.

[Results and Discussion]

After the PCR, the amplification states of PCR products were checked by agarose gel electrophoresis. The electrophoretic patterns were shown in FIG. 13 (left side). Also, the length of the PCR product was exactly determined by BIOANALYZER microfluidics platform (Agilent DNA12000 Kit). The electrophoretic patterns were shown in FIG. 14 (left side).

For comparison, results when the primer sets according to the present invention was used are present in the right side of each figure.

Figure 14:
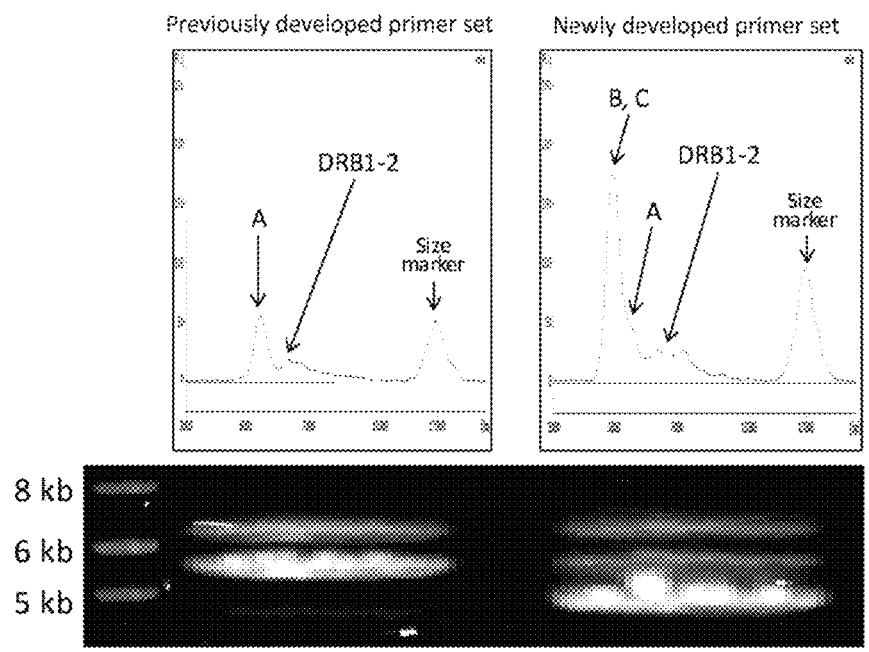
FIG. 14 Results regarding the lengths of multiplex PCR products of HLA-A, HLA-B, HLA-C and HLA-DRB1 genes amplified in Comparative Example 1 as measured by the bioanalyzer (upper drawing); and an agarose gel electrophoretic pattern thereof (lower drawing).

As seen in FIG. 14, when the primer sets described in the Patent Document 2 (previously developed primer sets) were used, HLA-B and HLA-C genes were not adequately amplified in a single tube wherein the primer sets specific to individual HLA-A, HLA-B, HLA-C and HLA-DRB1 genes were simultaneously contained. On the other hand, when the primer sets according to the present invention (newly developed primer sets) were used, all of the genes were amplified equally.

The invention claimed is:

1. A method for DNA typing of HLA in which phase ambiguity due to unclear cis/trans positional relationships is eliminated, or a null allele or a novel allele is detected, comprising the following steps:
   (1) a step of preparing sets of primers which respectively hybridize specifically to an upstream region and a downstream region of at least four genes comprising HLA-A, HLA-B, HLA-C, and HLA-DRB1 genes in a human genome sequence, and are capable of amplifying under the same PCR conditions wherein:
   the HLA-A gene is amplified by a primer set comprising an oligonucleotide comprising the nucleotide sequence as shown in SEQ ID NO: 1 or 2 and an oligonucleotide comprising the nucleotide sequence as shown in SEQ ID NO: 3;
   the HLA-B gene is amplified by a primer set comprising an oligonucleotide comprising the nucleotide sequence as shown in SEQ ID NO: 4 and an oligonucleotide comprising the nucleotide sequence as shown in SEQ ID NO: 5;
   the HLA-C gene is amplified by a primer set comprising an oligonucleotide comprising the nucleotide sequence as shown in SEQ ID NO: 6 or 7 and an oligonucleotide comprising the nucleotide sequence as shown in SEQ ID NO: 8; and
   the HLA-DRB1 gene is amplified by a primer set comprising an oligonucleotide comprising the nucleotide sequence as shown in SEQ ID NO: 9 and an oligonucleotide comprising the nucleotide sequence as shown in SEQ ID NO: 10, and/or a primer set comprising an oligonucleotide comprising the nucleotide sequence as shown in SEQ ID NO: 11 and an oligonucleotide comprising the nucleotide sequence as shown in SEQ ID NO: 12;
   (2) a step of simultaneously amplifying said at least four genes in a test sample (DNA) using the sets of primers in a single container under the same PCR conditions;
   (3) a step of sequencing the resulting PCR amplified products; and
   (4) a step of typing of said at least four genes at an 8-digit level by comparing with nucleotide sequences of known HLA alleles, wherein if said at least four genes are discriminated at an 8-digit level, typing without phase ambiguity is performed, or a null allele or novel allele, if present, is detected.

2. The method according to claim 1, wherein the PCR reaction comprises a warming step of 94° C. for 2 minutes, and 10 repetitions of a step consisting of a reaction at 98° C. for 10 seconds and a reaction at 68° C. for 5 minutes, and 20 repetitions of a step consisting of a reaction at 98° C. for 10 seconds and a reaction at 65° C. for 5 minutes.

3. The method according to claim 1, wherein the step of simultaneously amplifying said at least four genes comprises using one or more long range polymerases.

* * * * *

SEQUENCE LISTING

```
<160> NUMBER OF SEQ ID NOS: 31

<210> SEQ ID NO 1
<211> LENGTH: 32
<212> TYPE: DNA
<213> ORGANISM: Artificial Sequence
<220> FEATURE:
<223> OTHER INFORMATION: Synthesized Polynucleotide

<400> SEQUENCE: 1
cagaaactca gagctaagga atgatggcaa at                                    32

<210> SEQ ID NO 2
<211> LENGTH: 32
<212> TYPE: DNA
<213> ORGANISM: Artificial Sequence
<220> FEATURE:
<223> OTHER INFORMATION: Synthesized Polynucleotide

<400> SEQUENCE: 2
cagaaactca gagctatgga atgatggtaa at                                    32

<210> SEQ ID NO 3
<211> LENGTH: 30
```

```
<212> TYPE: DNA
<213> ORGANISM: Artificial Sequence
<220> FEATURE:
<223> OTHER INFORMATION: Synthesized Polynucleotide

<400> SEQUENCE: 3
gcatataacc atcatcgtgt cccaaggttc                                          30

<210> SEQ ID NO 4
<211> LENGTH: 29
<212> TYPE: DNA
<213> ORGANISM: Artificial Sequence
<220> FEATURE:
<223> OTHER INFORMATION: Synthesized Polynucleotide

<400> SEQUENCE: 4
ggttcccggt tgcaatagac agtaacaaa                                           29

<210> SEQ ID NO 5
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 5
acgggtccaa tttcacagac aaatgt                                              26

<210> SEQ ID NO 6
<211> LENGTH: 29
<212> TYPE: DNA
<213> ORGANISM: Artificial Sequence
<220> FEATURE:
<223> OTHER INFORMATION: Synthesized Polynucleotide

<400> SEQUENCE: 6
acactgctta gatgtgcata gttcacgaa                                           29

<210> SEQ ID NO 7
<211> LENGTH: 29
<212> TYPE: DNA
<213> ORGANISM: Artificial Sequence
<220> FEATURE:
<223> OTHER INFORMATION: Synthesized Polynucleotide

<400> SEQUENCE: 7
acactgctta gatgtgcata gttccggaa                                           29

<210> SEQ ID NO 8
<211> LENGTH: 40
<212> TYPE: DNA
<213> ORGANISM: Artificial Sequence
<220> FEATURE:
<223> OTHER INFORMATION: Synthesized Polynucleotide

<400> SEQUENCE: 8
gaacaattct agactatgga cccaatttta caaacaaata                               40

<210> SEQ ID NO 9
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 9
```
cgtttcctgt ggcagcctaa gagg                                         24

<210> SEQ ID NO 10
<211> LENGTH: 21
<212> TYPE: DNA
<213> ORGANISM: Artificial Sequence
<220> FEATURE:
<223> OTHER INFORMATION: Synthesized Polynucleotide

<400> SEQUENCE: 10
atgcacggga ggccatacgg t                                            21

<210> SEQ ID NO 11
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 11
cccacagcac gtttcttgga gtactc                                       26

<210> SEQ ID NO 12
<211> LENGTH: 22
<212> TYPE: DNA
<213> ORGANISM: Artificial Sequence
<220> FEATURE:
<223> OTHER INFORMATION: Synthesized Polynucleotide

<400> SEQUENCE: 12
gatgcacagg aggccatagg gt                                           22

<210> SEQ ID NO 13
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 13
cgcagcacgt tcttggagc tgcg                                          24

<210> SEQ ID NO 14
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 14
cgcagcacgt tcttggagc tgct                                          24

<210> SEQ ID NO 15
<211> LENGTH: 21
<212> TYPE: DNA
<213> ORGANISM: Artificial Sequence
<220> FEATURE:
<223> OTHER INFORMATION: Synthesized Polynucleotide

<400> SEQUENCE: 15
atgcacagga ggccataggg t                                            21

<210> SEQ ID NO 16
<211> LENGTH: 24
<212> TYPE: DNA
<213> ORGANISM: Artificial Sequence

```
<220> FEATURE:
<223> OTHER INFORMATION: Synthesized Polynucleotide

<400> SEQUENCE: 16
cacagcacgt tcttggagc aggc                                              24

<210> SEQ ID NO 17
<211> LENGTH: 21
<212> TYPE: DNA
<213> ORGANISM: Artificial Sequence
<220> FEATURE:
<223> OTHER INFORMATION: Synthesized Polynucleotide

<400> SEQUENCE: 17
atgcatggga ggcaggacag t                                                21

<210> SEQ ID NO 18
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 18
cacagcacgt tcttgcagc agga                                              24

<210> SEQ ID NO 19
<211> LENGTH: 21
<212> TYPE: DNA
<213> ORGANISM: Artificial Sequence
<220> FEATURE:
<223> OTHER INFORMATION: Synthesized Polynucleotide

<400> SEQUENCE: 19
atgcatggga ggccgtaggg t                                                21

<210> SEQ ID NO 20
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 20
gactgccagg gagggaaatc ract                                             24

<210> SEQ ID NO 21
<211> LENGTH: 25
<212> TYPE: DNA
<213> ORGANISM: Artificial Sequence
<220> FEATURE:
<223> OTHER INFORMATION: Synthesized Polynucleotide

<400> SEQUENCE: 21
gcgaatccag tggaggacac agcac                                            25

<210> SEQ ID NO 22
<211> LENGTH: 28
<212> TYPE: DNA
<213> ORGANISM: Artificial Sequence
<220> FEATURE:
<223> OTHER INFORMATION: Synthesized Polynucleotide

<400> SEQUENCE: 22
caaaccagaa gagaggctgg gatattct                                         28
```

<210> SEQ ID NO 23
<211> LENGTH: 32
<212> TYPE: DNA
<213> ORGANISM: Artificial Sequence
<220> FEATURE:
<223> OTHER INFORMATION: Synthesized Polynucleotide

<400> SEQUENCE: 23
aaccattagt attgcccta gtcactgtca ag                          32

<210> SEQ ID NO 24
<211> LENGTH: 29
<212> TYPE: DNA
<213> ORGANISM: Artificial Sequence
<220> FEATURE:
<223> OTHER INFORMATION: Synthesized Polynucleotide

<400> SEQUENCE: 24
cattagtact gcccctagtc actgccaag                             29

<210> SEQ ID NO 25
<211> LENGTH: 32
<212> TYPE: DNA
<213> ORGANISM: Artificial Sequence
<220> FEATURE:
<223> OTHER INFORMATION: Synthesized Polynucleotide

<400> SEQUENCE: 25
aaccattagt actgtcccta gtcactgcca ag                         32

<210> SEQ ID NO 26
<211> LENGTH: 29
<212> TYPE: DNA
<213> ORGANISM: Artificial Sequence
<220> FEATURE:
<223> OTHER INFORMATION: Synthesized Polynucleotide

<400> SEQUENCE: 26
cattagtact gcccctagtc actggcaag                             29

<210> SEQ ID NO 27
<211> LENGTH: 28
<212> TYPE: DNA
<213> ORGANISM: Artificial Sequence
<220> FEATURE:
<223> OTHER INFORMATION: Synthesized Polynucleotide

<400> SEQUENCE: 27
ggagctctct taaccacgct ggtaccta                              28

<210> SEQ ID NO 28
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 28
agctctcttg accacgctgg taccta                                26

<210> SEQ ID NO 29
<211> LENGTH: 28
<212> TYPE: DNA
<213> ORGANISM: Artificial Sequence
<220> FEATURE:
<223> OTHER INFORMATION: Synthesized Polynucleotide

```
<400> SEQUENCE: 29
ccattggcct cttggctata cctctttt                                            28

<210> SEQ ID NO 30
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 30
ctcagtgctc gcccctccct agtgat                                              26

<210> SEQ ID NO 31
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 31
gcacagtagc tttcgggaat tgacca                                              26
```